(12) United States Patent
Kim

(10) Patent No.: US 9,757,213 B2
(45) Date of Patent: Sep. 12, 2017

(54) HYBRID DENTAL IMPLANT

(71) Applicant: Ohio State Innovation Foundation, Columbus, OH (US)

(72) Inventor: Do-Gyoon Kim, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/704,295

(22) Filed: May 5, 2015

(65) Prior Publication Data
US 2015/0230889 A1    Aug. 20, 2015

Related U.S. Application Data

(63) Continuation-in-part of application No. 13/310,934, filed on Dec. 5, 2011, now abandoned.

(60) Provisional application No. 61/419,333, filed on Dec. 3, 2010.

(51) Int. Cl.
*A61C 8/00* (2006.01)

(52) U.S. Cl.
CPC .......... *A61C 8/0022* (2013.01); *A61C 8/0037* (2013.01)

(58) Field of Classification Search
CPC ... A61C 8/0018; A61C 8/0024; A61C 8/0022; A61C 8/0037; A61C 8/00; F16B 2/065; F16B 5/0072; F16B 5/0004; F16B 25/00; F16B 19/08; F16B 2019/1009; F16B 2019/1018; F16B 7/18
USPC ...... 433/172–176, 201.1, 39, 135, 137, 138, 433/148, 149, 150, 153, 155, 156, 162; 606/156, 157, 158, 304; 604/506, 174, 604/20, 501
See application file for complete search history.

(56) References Cited

U.S. PATENT DOCUMENTS

| 5,192,282 | A |   | 3/1993  | Draenert |
|-----------|---|---|---------|----------|
| 5,366,374 | A | * | 11/1994 | Vlassis ............... A61C 8/0018 433/165 |
| 6,048,204 | A |   | 4/2000  | Klardie et al. |
| 6,755,835 | B2| * | 6/2004  | Schultheiss ........ A61B 17/8685 606/304 |

(Continued)

OTHER PUBLICATIONS

Blanes, R.J., et al.; A 10-Year Prospective Study of ITI Dental Implants Placed in the Posterior Region, I: Clinical and Radiographic Results; Clin. Oral Implants Res., Dec. 2007, vol. 18(6); pp. 699-706.

(Continued)

*Primary Examiner* — Cris L Rodriguez
*Assistant Examiner* — Mirayda A Aponte
(74) *Attorney, Agent, or Firm* — Meunier Carlin & Curfman LLC

(57) ABSTRACT

The present invention provides for a hybrid dental implant having a screw body with at least one external thread, which includes an upper portion with an open ceiling configured to receive one or more bone inducing agents and/or therapeutic agents, a middle portion having a hollow inner channel connected to side openings, and a lower portion with a closed floor. The bone inducing agents and/or therapeutic agents are introduced through the open ceiling into the hollow inner channel into the side openings, which enables the bone tissue ingrowth into the hollow inner channel and bone tissue outgrowth from the hollow inner channel to the surrounding bone. It also provides for a method of installing and using the hybrid dental implant thereof.

15 Claims, 13 Drawing Sheets

(56) References Cited

U.S. PATENT DOCUMENTS

2008/0119945 A1    5/2008  Frigg
2011/0060373 A1*   3/2011  Russell .............. A61B 17/0401
                                                          606/304
2013/0011814 A1    1/2013  Battula

OTHER PUBLICATIONS

Kim, D.G., et al.; Bone Ingrowth and Initial Stability of Titanium and Porous Tantalum Dental Implants: A Pilot Canine Study; Implant Dent., Aug. 2013, vol. 22(4), pp. 399-405.

Seong, W.J., et al.; Ex Vivo Mechanical Properties of Dental Implant Bone Cement Used to Rescue Initially Unstable Dental Implants: A Rabbit Study; Int. J. Oral. Maxillofac Implants, Jul.-Aug. 2011, vol. 26(4), pp. 826-836.

Wang, Xiupeng et al.; Effects of Additives on the Rheological Properties and Injectability of a Calcium Phosphate Bone Substitute Material; Journal of Biomedical Materials Research Part B: Applied Biomaterials; Dec. 16, 2005; pp. 259-264; Wiley InterScience, Wiley Periodicals, Inc.

Lye, Kok Weng et al.; Bone Cements and Their Potential Use in a Mandibular Endoprosthesis; Tissue Engineering: Part B; 2009; pp. 485-497; vol. 15, No. 4; Mary Ann Liebert, Inc.

Boger, Andreas et al.; Properties of an Injectable Low Modulus PMMA Bone Cement for Osteoporotic Bone; Journal of Biomedical Materials Research Part B: Applied Biomaterials; Feb. 20, 2008; pp. 474-482; Wiley InterScience, Wiley Periodicals, Inc.

Peterson, Larry J. et al.; Clinical, Radiographical and Histological Evaluation of Porous Rooted Polymethylmethacrylate Dental Implants; J. Dent. Res.; Jan. 1979; pp. 489-496; vol. 58(1).

Venuleo, Caterina et al.; Long Term Bone Level Stability on Short Implants: A Radiographic Follow Up Study; Journal of Maxillofacial & Oral Surgery; 2008; pp. 340-345; vol. 7; No. 3; www.jmosi.com.

Gisep, A. et al.; Augmentation of Implant Purchase with Bone Cements: An In Vitro Study of Injectability and Dough Distribution; Oct. 21, 2005; pp. 114-119; Wiley InterScience, Wiley Periodicals, Inc.

Mulder, L. et al.; Relationship between Tissue Stiffness and Degree of Mineralization of Developing Trabecular Bone; J. Biomed Mater Res A; Feb. 2008; 84(2):pp. 508-515; Wiley Interscience, Wiley Periodicals, Inc.

* cited by examiner

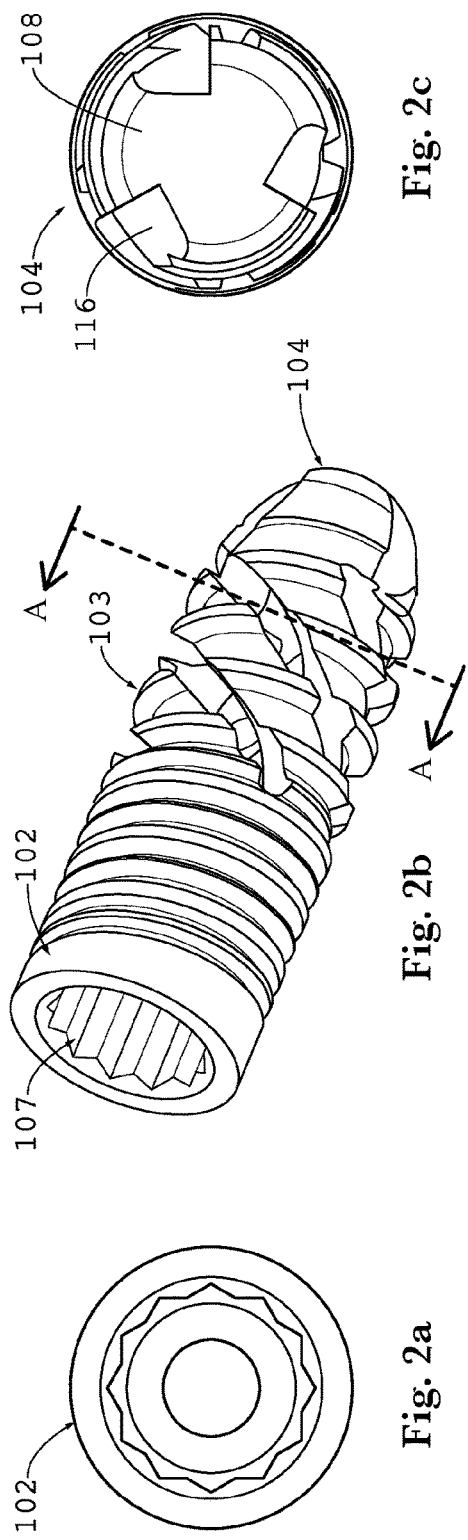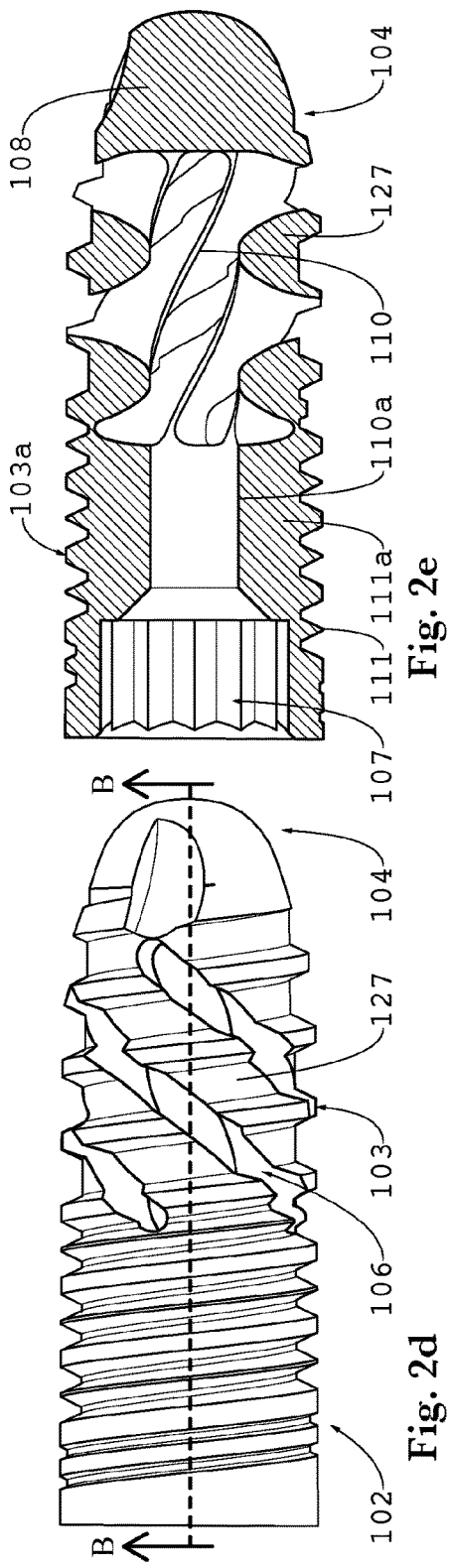

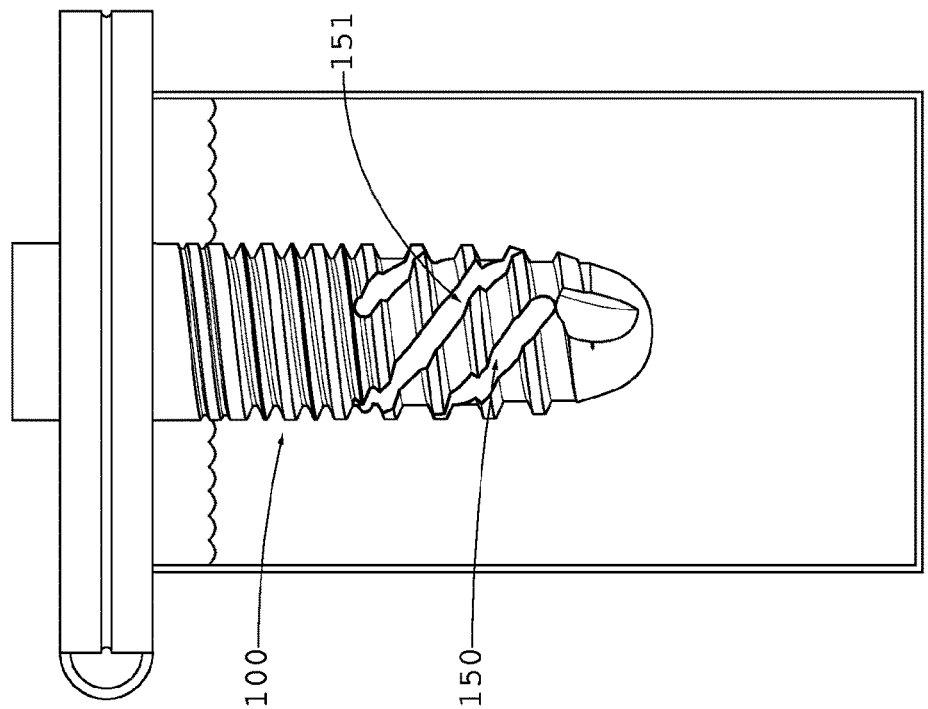
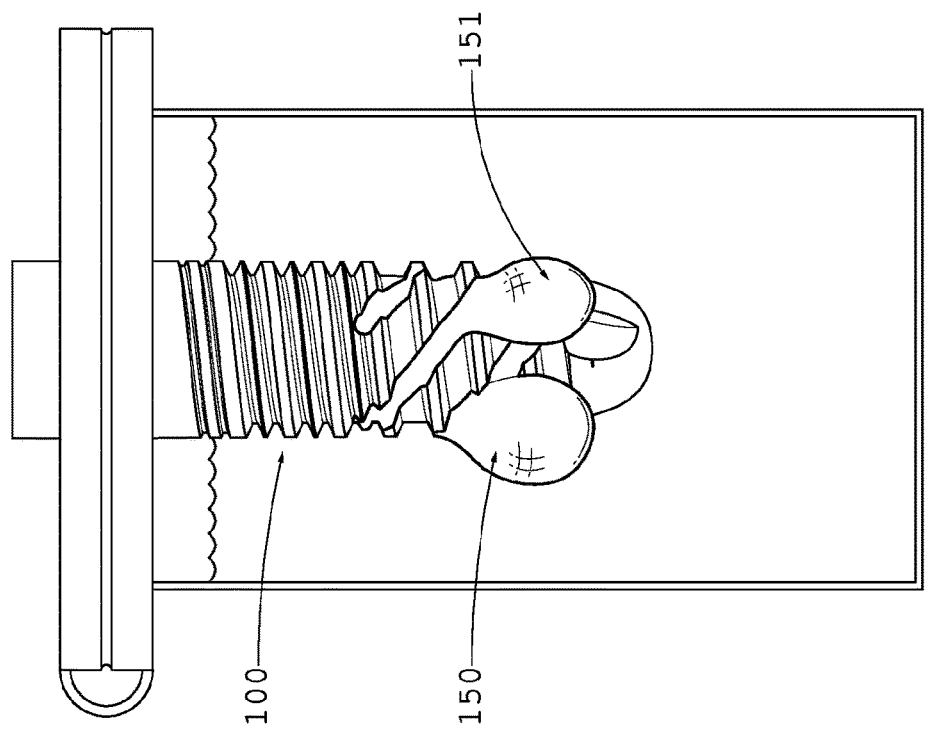

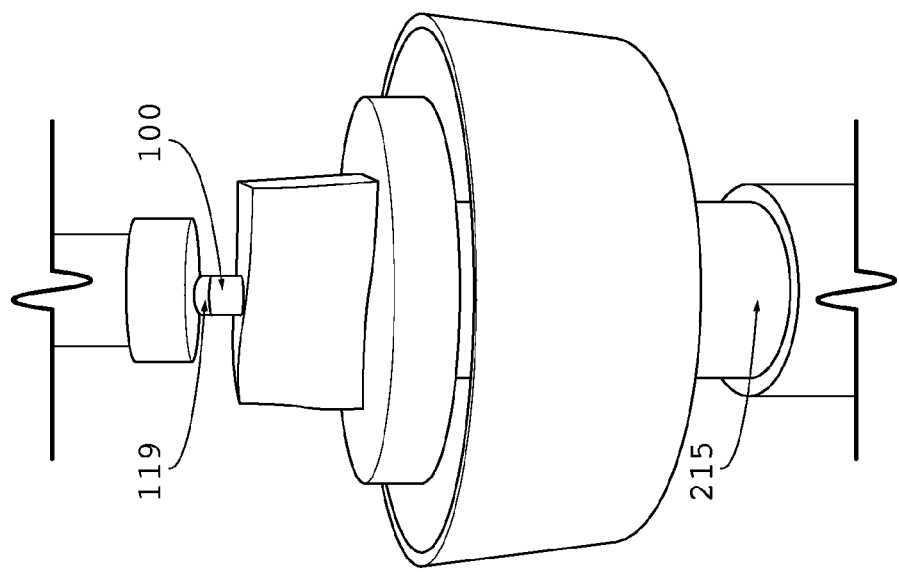
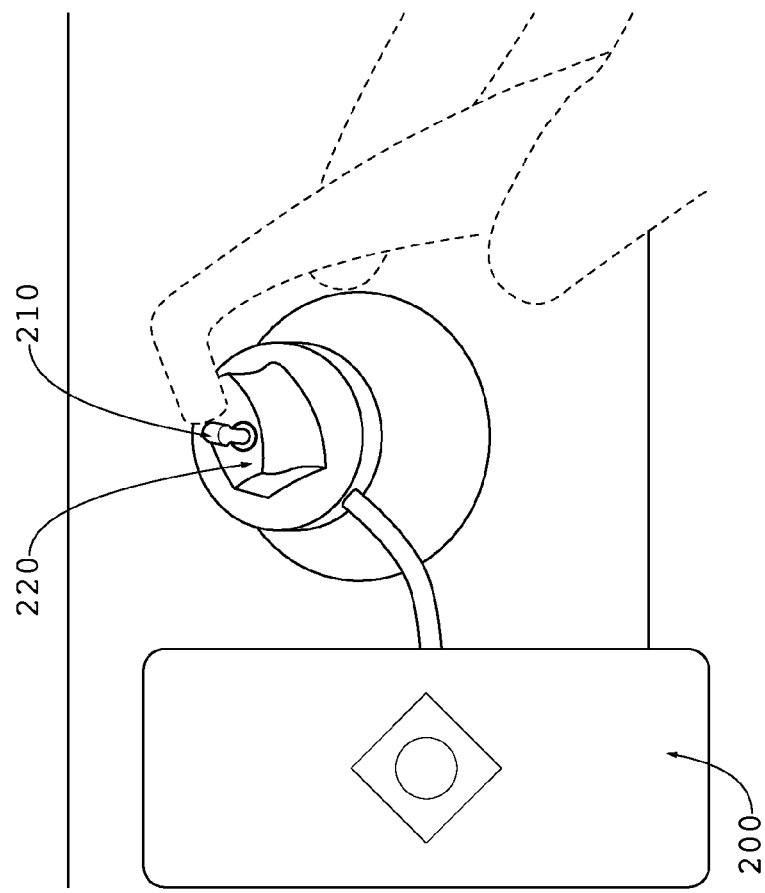
Fig. 6b
Fig. 6a

HYBRID DENTAL IMPLANT

CROSS-REFERENCES TO RELATED APPLICATIONS

This application is a continuation in part patent application to the U.S. patent application Ser. No. 13/310,934 filed on Dec. 5, 2011, which claims benefit of the U.S. Provisional Patent Application No. 61/419,333 filed on Dec. 3, 2010. Both the U.S. patent application Ser. No. 13/310,934 and the U.S. Provisional Patent Application No. 61/419,333 are hereby incorporated by reference in their entirety.

STATEMENT REGARDING FEDERALLY-SPONSORED RESEARCH AND DEVELOPMENT (Not Applicable)

THE NAMES OF THE PARTIES TO A JOINT RESEARCH AGREEMENT (Not Applicable)

REFERENCE TO AN APPENDIX (Not Applicable)

FIELD OF THE INVENTION

This invention relates generally to the field of dental implants that provide bone tissue augmentation or bone regeneration to promote osseointegration.

BACKGROUND OF THE INVENTION

Currently, a dental implant is a "root" device used in dentistry to support restorations that resemble a tooth or group of teeth to replace missing teeth. The dental implants, abutments, and dental prostheses are collectively called dental restorations or implant systems that resemble a tooth or group of teeth (referred to as "restoration" or "implant system") as replacements for missing teeth. A dental implant generally appears similar to an actual tooth root and is placed within the bone of the jaw to replace the root of the missing tooth. After the implant surface fuses with the surrounding jaw bone (osseointegration), dental abutments and other dental prostheses, such as crowns, implant-supported bridges or dentures, can be installed. The dental abutments and prostheses then allow a patient to use the restorations for chewing (also called masticatory loading).

The process of placing the dental implants into the jaw bone of a patient is called dental implantation, and it is a very vigorous surgical procedure, resulting in bone damage at the bone-implant interface. A relatively long healing period follows this dental implantation process, which lasts at least about two to three months and may extend to six months. During the healing period, (1) the bone damage is repaired and replaced with new bone tissues (active biological bone remodeling); and (2) direct bone ingrowth or fusion between the implant surface and the bone tissue surrounding the implant is also achieved (osseointegration). If the healing time is too short before any masticatory force is applied on the implant, the implant might risk failure because of the bone damage in the pre-existing interfacial bone, weak new bone tissues, and unstable bone-implant interface with partial osseointegration. The masticatory force applied on an insufficiently healed implant creates excessive micro-motion between bone and implant surface, resulting in fibrous tissue development at the interface which might block further osseointegration and cause eventual failure of the implant system.

To prevent or reduce any possible direct masticatory force being applied on the implant, the installed implant is protected under a healing cap during the healing period. After a sufficient healing period, a second surgery is conducted to install an abutment and prosthesis (artificial tooth crown). The combination of these two surgeries results in an implant system that is regarded as a dental replacement for the missing tooth.

Most patients who need dental implantation have various levels of bone deficiency due to oral bone complications that cause the initial extraction of teeth and bone loss following extraction. For example, tooth extraction and disuse atrophy arising from delayed treatment can lead to loss of the alveolar ridge. Segmental oral reconstruction surgeries are likely to result in substantial defects and disconnections in the mandibular bone. A posterior maxillary tooth extraction occasionally produces too thin sinus floor. Often, bone augmentation is required to place implants in oral bone sites with too severe a bone defect.

Bone grafting surgery is a popular method to treat the bone deficiency in many critical oral defects. Autologous bone has been accepted as an ideal material for grafting allogeneic grafts, which is obtained from human cadavers and animals. However, these bone materials bring the risks of infection and immune rejection. In addition, the degree of bone incorporation or growth through the bone grafting process is uncertain and unclear. Further, many clinical cases reported post-implantation failures at the bone grafted sites after the bone grafting process. In addition, the grafting for bone augmentations imposes additional surgical steps for patients, increasing the overall treatment costs.

Many studies indicated that growth factors can be introduced to induce bone augmentation, and it has been suggested that bone morphogenetic protein (BMP) has the most potent ability for stimulating bone growth. However, a high BMP dose was shown to cause uncontrolled progress of bone augmentation next to the implant. Substantial marginal bone loss adjacent to implants can arise from oral bone disease, including osteoporosis and peri-implantitis under high impact loading of static occlusion and dynamic mastication. Revision surgeries are often required to treat these post-implantation complications. Thus, development of a new implantation strategy that can minimize the additional pre- and post-implantation surgeries is needed.

BRIEF SUMMARY OF THE INVENTION

There exists a need to have a dental implant system that allows for simultaneous bone augmentation, and if needed, any post-implantation treatments. The present invention meets this need by providing a hybrid dental implant that is simple, inexpensive, and easy-to-use. This dental implant allows for injection of the effective bone inducing agents to accelerate bone regeneration, and preferably, able to treat oral complication associated with the implant without surgical intervention, while the implant system maintains its role in bearing masticatory loading after the implantation process. That is, the hybrid dental implant functions both as a dental implant and as a functional scaffold for bone augmentation agents or other medical agents to enhance bone regeneration within and around the dental implant during the post-implantation healing period without any additional surgeries. As such, the hybrid dental implant provides a better long-term mechanical stability of the implant system. For purposes of this invention, the bone inducing agent can also be referred to as "bone growth factors," including one or more bone morphogenetic proteins (BMP).

The hybrid dental implant includes a screw body with one or more external threads. The screw body has an upper portion with an open ceiling, a middle portion having a hollow inner channel, and a lower portion with a closed floor. The hollow inner channel is connected to the open ceiling to enable it to receive one or more injectable bone growth agents. In some embodiments, additional medical agents can be include prior to, during, or after dental implantation. Preferably, the hollow inner channel has a diameter in the range of about 0.5 mm to about 2.0 mm, preferable in the range of about 1.0 mm to about 1.5 mm.

The side openings extend from the hollow inner channel, rotating in an angle across a plurality turns of the external thread into a longitudinal direction, the angle being in a range of 30° to 60°, preferably 25° to 50°, relative to the turns of the external thread. The dimensions of the side openings are of a size designed to enable bone or bone tissue ingrowth into the hollow inner channel and bone outgrowth from the hollow inner channel to the surrounding bone. Preferably, the side openings are of a helix-like construction (FIGS. 1 to 4), having rotating planes 125 in the longitudinal direction 21 along the longitudinal axis 20 and in the radial direction 25. In the radial direction, the rotating planes are substantially parallel to each other with the width at the inner surface of the screw body substantially the same as the width at the outer surface of the screw body. The widths 115 of the rotating planes 125 of the side opening is preferably in the range of about 0.6 mm to 1.5 mm.

Preferably, the upper portion, the middle portion, and the lower portion of the screw body located successively along the length of the screw body in a longitudinal direction, the upper portion occupying the upper 40% to 50% of the length of the screw body, the middle portion adjacent to the upper portion occupying the middle 40% to 50% of the length of the screw body, and the lower portion is adjacent to the middle portion, occupying the lower 10% to 20% of the lower or bottom portion of the length of the screw body.

Preferably, the lower portion has a conical shape, and has one or more self-tapping cuts at a front end of the lower portion.

Preferably, the upper portion further comprises a plug-in screw connected to the opening ceiling, extending into the hollow inner channel to enable addition of subsequent doses of bone inducing agents and/or therapeutic agents after the implantation.

The bone inducing agents preferably include one or more bone morphogenetic proteins. The bone inducing agents are preferably loaded onto a hydrogel, which can then be injected or introduced into the hollow inner channel prior to, at, and/or after the implantation. The bone inducing agents and/or therapeutic agents can be injected or introduced into the hydrogel after the implantation periodically without additional surgeries. The combination of the loaded hydrogel and the dental implant provides a dental implant system that allows for controlled delivery of bone inducing agents and other therapeutic agents to enable bone regeneration in a controlled fashion to allow for bone ingrowth into the hollow inner channel and bone outgrowth from the hollow inner channel into the surrounding bone.

The present invention also includes a method for installing a hybrid dental implant into a bone. The method includes the steps of (a) screwing a hybrid implant with a screw body having at least one external thread into a bored hole in the bone, and (b) injecting a suitable amount of bone inducing agent loaded hydrogel into an open ceiling of the implant, thereby pushing the hydrogel into the upper portion of the implant, whereby the hydrogel moves into a hollow inner channel in a middle portion of the implant with one or more side openings, through which the bone inducing agent enables bone ingrowth into the hollow inner channel. Preferably, the medical or therapeutic agents are injected into the hollow inner channel subsequently, which can be during the implantation and/or after the implantation. Preferably, after waiting a period of time post-implantation, one or more doses of bone inducing agents can be injected into the hydrogel into the hollow inner channel. Additionally, one or more therapeutic agents can be introduced into the hollow inner channel during and/or after the implantation.

BRIEF DESCRIPTION OF THE SEVERAL VIEWS OF THE DRAWINGS

FIG. 2a is a top view illustrating the dental implant of FIG. 1. FIG. 2b is an isometric side view illustrating the dental implant of FIG. 1. FIG. 2c is a bottom section view illustrating the dental implant through the line A-A of FIG. 2b. FIG. 2d is a side view illustrating the dental implant of FIG. 1. FIG. 2e is a central section view illustrating the dental implant of FIG. 1 through the line B-B of FIG. 2d.

FIG. 5a illustrates the injection of bone inducing agents (or bone growth factors) loaded hydrogels into the implant of FIG. 1 in a blood analog solution immediately after the injection. FIG. 5b illustrates the injection of bone inducing agents (or both growth factors) loaded hydrogels into the implant of FIG. 1 in a blood analog solution after partial degradation.

FIG. 6a illustrates a Resonance Frequency Analysis (RFA) 200 with a transducer 210 mounted on the top of an implant in bone block 220. FIG. 6b illustrates the dental implant system 100 with a healing cap 119 subjected to DMA using a loading machine with a load cell 215.

Figure 1:
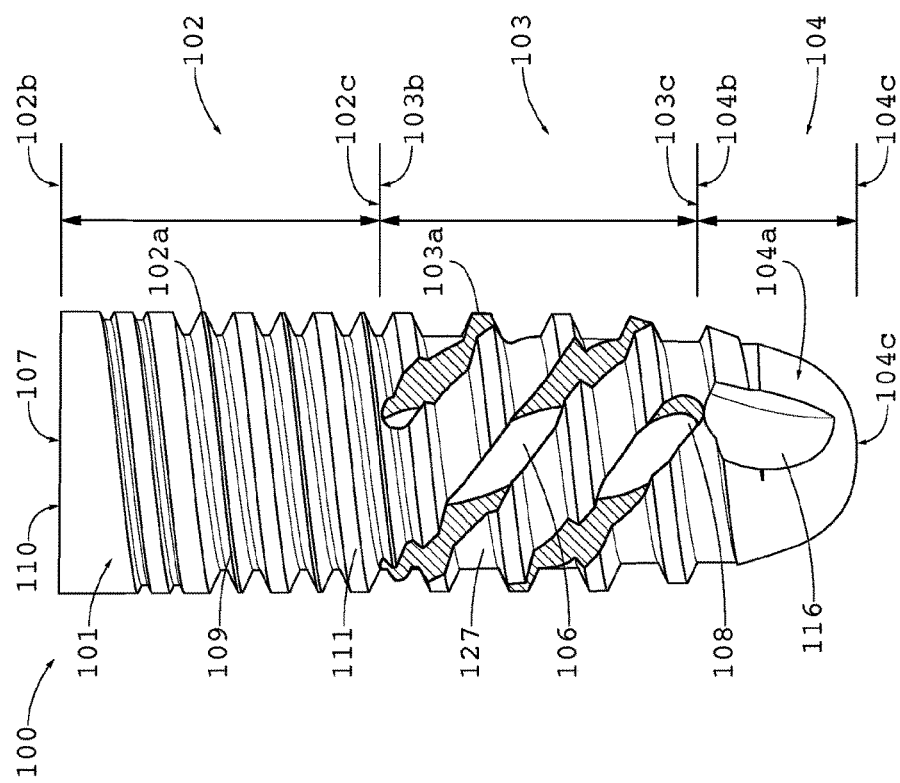
FIG. 1 shows a perspective view of an embodiment of a dental implant in accordance with the invention.
Figure 3B:
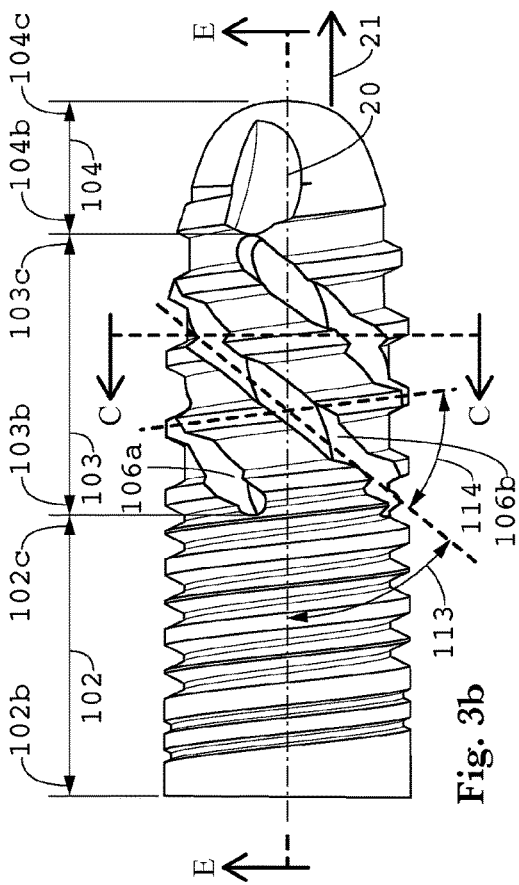
FIG. 3b is a side view illustrating the dental implant of FIG. 1.
Figure 3C:
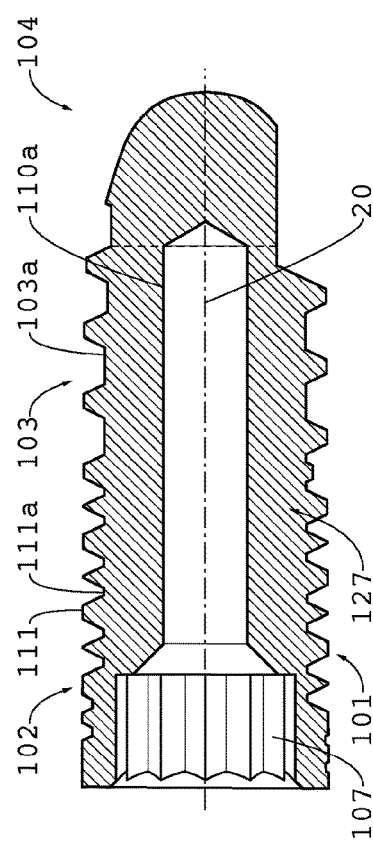
FIG. 3c is a side view in section illustrating the dental implant through the line E-E of FIG. 3b.
Figure 3A:
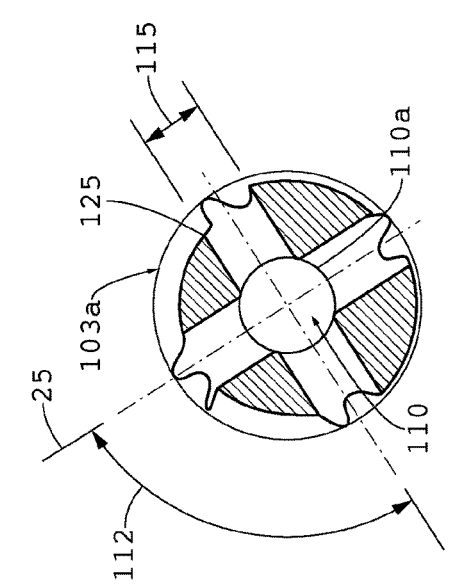
FIG. 3a is a top view in section illustrating the dental implant of FIG. 1 through the line C-C of FIG. 3b.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

Broadly, the present invention provides for a hybrid dental implant with a hollow inner channel with one or more side openings, a screw body with an upper portion, a middle portion upon which the side openings are situated, and a lower portion. Through the hollow inner channel, bone inducing agent and other medication can be introduced into the screw body, and with the side openings, the bone regeneration or augmentation can be achieved inside of the hollow inner channel and from the hollow inner channel to the surrounding bone, promoting osseointegration of the dental implant in normal, more preferably the bone deficient sites. The implant preferably has a screw body of any suitable shape with one or more external threads. In addition, the implant surfaces may be modified by plasma spraying, anodizing, etching, or sandblasting to increase the surface area and osseointegration potential of the implant.

Preferably, the body of the dental implant 100 (as shown in FIGS. 1 to 4) has a screw shape body 101 with at least one external thread 109 with a plurality of turns rotating, preferably substantially symmetrically, relative to the longitudinal axis 20. The screw body 101 has an upper portion 102, a middle portion 103, and a lower portion 104 successively in the longitudinal direction of the screw body 101. The upper portion 102 has an open ceiling 107 configured to receive one or more injectable bone inducing agents, preferably also to include other medicinal agents, such as anti-inflammatory therapeutic agent (anti-TNF-α-antibody). The upper portion 102 extends in the longitudinal direction 21 from the upper end 102b of the screw body 101 to the lower end 102c of the upper portion. Preferably, the upper portion 102 occupies the upper 40 to 50% of the length of the screw body 101, starting from the upper end 102b and ending to the lower end 103c of the upper portion 102, as shown in FIG. 1. For example, the upper portion 102 can have a length in the longitudinal direction in the range of about 4 mm to 5 mm. The middle portion 103 ranges from the upper end 103b of the middle portion 103, which is close to or adjacent to the lower end 102c of the upper portion 102, to the lower end 103c of the middle portion 103, occupying the middle 40 to 50% of the length of the screw body subsequent to the upper portion 102 in a longitudinal direction. The beginning end 106a of the side opening 106 is adjacent to or close to the beginning end 103b of the middle portion 103; while the lower end 106b of the side opening 106 is closed to or at the lower end 103c of the middle portion 103. The lower portion 104 ranges from the upper end 104b of the lower portion 104 to the ending tip (or lower end) 104c of the lower portion 104, occupying about 10% to about 20% of the bottom or lower length of the screw body 101. The closed floor 108 is adjacent to or at the beginning end 104b of the lower portion 104. The outer surfaces 102a and 103a of the upper portion 102 and the middle portion 103 are cylindrical and coaxial relative to the longitudinal axis 20. The outer surface 104a of the lower portion 104 is preferably in a conical shape with a tapered ending as shown in FIGS. 1 to 4.

The middle portion 103 has the hollow inner channel 110 with one or more helix-shaped side openings 106, wherein the hollow inner channel 110 extends to the open ceiling. The hollow inner channel 110 is shaped to allow injectable bone inducing agent to be introduced through the opening ceiling 107 of the upper portion 102 of the screw body 101 into the side openings 106 embedded in the middle portion 103, and the hollow inner channel 110 terminates at the closed floor 108 at the lower portion 104. The hollow inner channel 110 is enveloped by a shell 127, which extends from the outer perimeter 110a of the hollow inner channel 110 (which is an inner surface of the middle portion) to the outer surface 103a of the middle portion 103, which accounts for the thickness of the shell 127. The outer surface 103a of the middle portion 103 is composed of the turns 111 of the external threads 109 and the spaces 111a between the turns of the external threads 109. The diameter of the hollow inner channel (also referred to as the size of the outer perimeter 110a of the hollow inner channel 110) is preferably in a range of about 0.5 to about 2.0 mm, preferably in a range of 1.0 mm to 1.5 mm. The shell 127, preferably, has a thickness at least about 2 mm to about 5 or 6 mm depending on the size of the implant. A typical dental implant size is about 3.5 mm to 5.0 mm wide and about 10 mm to 15 mm long.

The side openings 106 extend angularly in a radial direction 25 and in a peripheral direction from the hollow inner channel 110 in the middle portion 103, and transverse across a plurality of turns 111 of the external thread 109 in an angle relative to the longitudinal axis 20. Preferably, the side opening 106 rotates around the longitudinal axis 20 in the longitudinal direction 21 in the middle portion 103 at an angle 113 relative to the longitudinal axis 20, preferably in a range of 25° to 50°, most preferably at 45°, and at an angle 114 relative to the turns 111 of the external thread 109 in a range of 30° to 60°, preferably in a range of 25° to 50°, most preferably at 45°. The subsequent rotating turns 106a, 106b of the side opening 106 stretch from each other in a peripheral direction in an angle 112 in a range of 70° to 100°, preferably in an angle 112 of about 90° (see FIG. 3(a)). Preferably, the side openings are of a helix-like construction (FIGS. 1 to 4), having rotating planes 125 in the longitudinal direction 21 along the longitudinal axis 20 and in the radial direction 25. In the radial direction, the rotating planes are substantially parallel to each other with the width at the inner surface of the screw body substantially the same as the width at the outer surface of the screw body. The widths 115 of the rotating planes 125 of the side opening is preferably in the range of about 0.6 mm to 1.5 mm.

Preferably, the side openings are of a helix-like construction (FIGS. 1 to 4), having rotating planes 125 in the longitudinal direction 21 along the longitudinal axis 20 and in the radial direction 25. In the radial direction, the rotating planes are substantially parallel to each other with the width at the inner surface of the screw body substantially the same as the width at the outer surface of the screw body. The widths 115 of the rotating planes 125 of the side opening are preferably in the range of about 0.6 mm to 1.5 mm. That is, the width 115 is about 0.6 mm or larger, but less than 1.5 mm, preferably in the range of 0.7 to 0.9 mm, and in some embodiments, the width 115 is about 0.79 mm. In some embodiments, there is one side opening 106 with multiple turns, 106a, 106b, etc., preferably rotating in the middle portion 103 of the screw body 101 in the manner of a single-stranded helix (FIG. 2). In some other embodiments, two or more side openings 106 twisted along the shell 127 of middle portion The dimensions of the side openings 106 are designed such that that they enable the bone inducing agents to induce bone tissue regeneration, promoting bone ingrowth through the side openings 106 into the hollow inner channel 110 and bone outgrowth from the hollow inner channel 110 to the surrounding bone so that the bone contact at the implant site is restored or augmented sufficiently for osseointegration to enable for successful implantation of the hybrid implant 100. At the same time, the dimensions of the side openings 106 are designed to maintain the stability of the implant 100 so that the implant 100 can withstand the impact of insertion into the dental implant site and subsequent masticatory loading from chewing. The stability of the implant 100 can be accounted clinically via the stability quotient (ISQ) value of Resonance Frequency Analysis (RFA) 200, which is assessed by using dynamic mechanical analysis (DMA) (as shown in FIG. 6). FIG. 6 shows (a) a RFA 200 with a transducer 210 mounted on the top of an implant in bone block 220 and (b) then the dental implant system 100 with a healing cap 119 were subjected to DMA using a loading machine with a load cell 215.

In other words, the side openings are designed to deliver effective agents to induce bone regeneration. It is anticipated that bone ingrowth into the openings occurs while simultaneously integrating the implant threads. The side openings transverse across the implant threads in an angle ranging from 30° to 60° relative to the turns of the thread, the hollow inner channel having a diameter in the range of about 0.5 mm to about 2.0 mm, and sufficient turns and spacing of the implant threads between openings are maintained to allow for bone tissue regeneration while maintaining structural stability to sustain bone implantation.

Moreover, the hybrid implant system can be used as an excellent scaffold or drug delivery device for bone regeneration and other medical treatment during the post-implantation healing period, which will provide for a better long-term mechanical stability of the implant system. This implant system also shows that it passes the mechanical testing following the international standard (ISO 14801) as required by food and drug administration (FDA) regulations.

The dental implant of the present invention may be made of titanium or other suitable biocompatible materials. Titanium is a preferred material because the bone is observed to adhere to titanium surfaces ("osseointegration"). Suitable titanium can be pure titanium or a titanium alloy. Commercially pure titanium is available in four grades depending upon the amount of carbon and iron contained therein. The commercially available titanium alloy is grade 5 titanium, Titanium 6AL-4V (signifying the titanium alloy containing 6% aluminum and 4% vanadium), which offers similar osseointegration levels as that of commercially pure titanium with better tensile strength and fracture resistance.

The implant 100 is intended to be inserted into a bored hole in the jaw bone for permanent anchoring of artificial teeth, tooth-bridges and other dental prostheses. The insertion starts with screwing the lower portion 104 of the implant into the bore hole until the entire implant, including the upper portion 102, is screwed into the bore hole of the bone. Preferred shapes of the dental implant are the shapes which assist in the insertion of the implant, such as substantially frustoconical, substantially cylindrical (FIGS. 1c-1e), or any other suitable shape(s). For example, frustoconical shape with tapering threads allows the front end to be screwed into the pre-prepared bone hole more easily and provides for tighter insertion or coupling with the bone initially. Therefore, the initial tight coupling of the outer threaded parts of the implant with the adjacent bone provides for the initial mechanical stability of the implant during the healing period. For the purpose of this invention, the bone cement is added to augment this initial stability. The outer threaded parts of the implant can be called "the threaded parts of the implant," "implant thread," or "screw thread" interchangeably.

Figure 4:
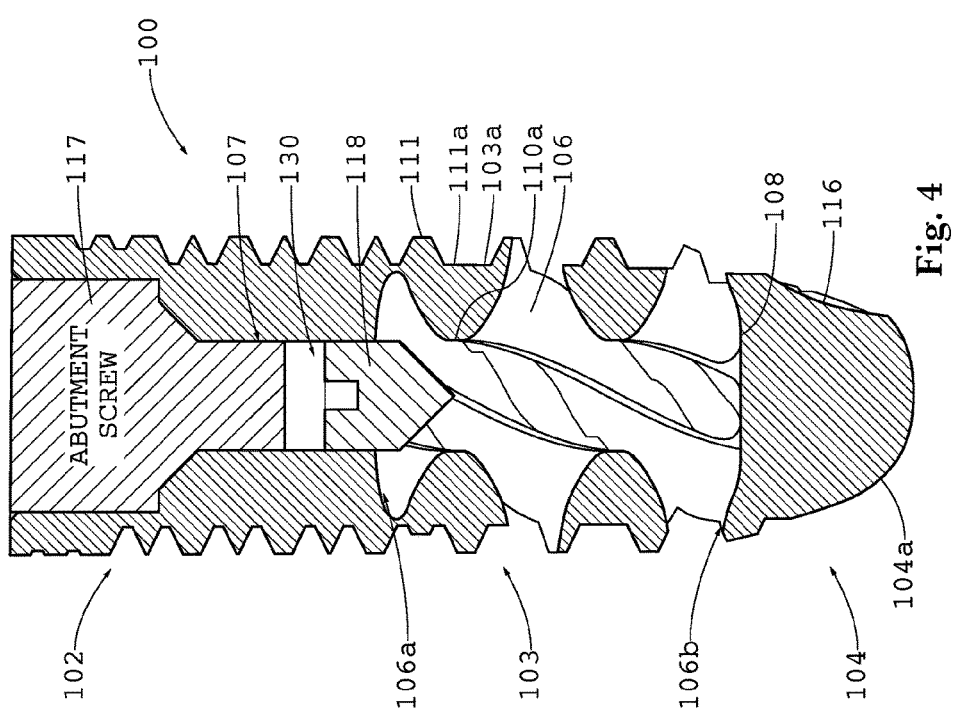
FIG. 4 shows a lateral sectional view of the dental implant of FIG. 1 having an abutment screw 117 set in place.

The upper portion 102 has an optional collar and an attachment means for attaching a dental prosthesis thereto. As shown by FIGS. 1-4, the attachment means is the open ceiling 107 within the upper portion 102, through which bone inducing agents and/or other medicinal agents can be introduced. The open ceiling is preferably threaded to accept threaded inserts, such as an abutment screw 117 and an additional plug-in screw 118 below the abutment screw 117 to prevent unwanted subject invading through the hollow inner channel 110 during implantation surgery, as shown in FIG. 4. This double screw system can prevent any infection through the hollow inner channel when the abutment screw is loosened during post-implantation therapeutic agent loading (discuss later). The plug-in screw 118 can be easily unplugged whenever injection of a therapeutic agent or bone inducing agent is needed. There is a gap 130 between the abutment screw 117 and the plug-in screw 118, which disconnects direct transferring of the load from the abutment screw 117 to the plug-in screw 118 to decrease the risk of loosening of the plug-in screw 118. Antibiotics (one type of therapeutic agent) can be filled in the gap space 130 between the abutment screw 117 and the plug-in screw 118. The combination of the abutment screw 117 and the plug-in screw 118 can act together in some ways as a longer healing cap screw (can also be referred to as "healing cap") except for the double screw system has additional advantages such as the gap space 130. Similar to the tapered end of the healing cap screw 119 in FIG. 12, the tapered end of the plug-in screw 118 expands into the hollow inner channel, which can help deliver injected agents by making a path 140 through the regenerated bone tissue in the hollow inner channel after implantation.

The lower portion 104 of the implant preferably has one or more self-tapping cuts 116 at the front end of the lower portion 104 with a tapering conical shape, which facilitate the insertion of the implant into the bored hole in the bone tissue. The tapering cuts can be longitudinal cavities having cutting faces with cutting edges to provide self-tapping. A cutting edge may have a plurality of cutting teeth. Other suitable types of self-tapping cuts can also be used. In addition, these cutting edges can provide more implant-bone interface area for osseointegration.

The present invention also provides a method for installing a hybrid dental implant into bone, which includes the following steps: First, screwing a hybrid implant with a screw body having at least one external thread into a bored hole in the bone. Then, injecting a suitable amount of injectable bone inducing agents, such as BMP (bone morphogenetic protein), into an open ceiling of the implant, thereby pushing the bone inducing agent into an upper portion of the implant. The bone inducing agent moves through a hollow inner channel, which is formed of an inner cavity in communication with the open ceiling, into a middle portion of the implant having one or more side openings. Preferably, the hollow inner channel retains most of or all of the bone inducing agent, while side openings allow for bone ingrowth into the hollow inner channel.

Once a suitable amount of the bone inducing agent is introduced into the implant and into the surrounding bone, the rest of the implant or restoration system can be installed in the same surgical procedure by adding the following steps: waiting for a period of time sufficient to allow for the osseointegration and sufficient bone regeneration, and then, attaching a dental abutment and/or prosthesis to the implant.

The process of "inserting the hybrid dental implant into a bone" typically has two steps: (1) boring a pilot hole of an appropriate depth into the dental patient's jaw bone; and then (2) screwing the implant into place in the pilot hole, preferably using a self-tapping cut or cuts of the lower portion.

After the implant is inserted into bone, the bone inducing agent is injected into the open ceiling 107 of the hollow inner channel 110 of the implant by using a suitable syringe. Through the hollow inner channel, the bone inducing agent is pushed and/or moved into the middle portion, some of which spread through the side openings 106 into the cracks and/or spaces of the surrounding bone generated during the above installation (also called implantation). The neck fitting of the syringe preferably has an outer diameter adapted to fit into the open ceiling 107, usually around 0.5 mm to 2 mm diameter.

In some preferred embodiments, one or more bone inducing agents 153 and/or therapeutic agents 154 (collectively called "agents" 151) are first loaded into a hydrogel 150, and then the agents loaded hydrogel 150 is delivered into the hollow inner channel 110 of the implant through the open ceiling 107. Then after the implantation, additional agents can be injected to promote further bone regeneration. For purposes of the present invention, the term "agent" refers to both bone inducing agents and therapeutic agents. Therapeutic agents include antibiotics, anti-inflammatory agents, and other agents having therapeutic benefits to human in preventing or combating diseases. In this embodiment, the implantation can act as a controlled delivery device for optimum bone regeneration and for effective drug or therapeutic agent delivery.

A hydrogel is a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content. Often, it can be hardened or remain semi-liquid to provide sustained release profile. The implant of the present invention enables the use of such hydrogen without compromising the mechanical stability of the implant.

Preferably, the gel type of carrier includes demineralized bone matrix (DMB) or other types of the bone inducing agents (such as rhBMP-2 proposed in Example 5) along with platelet gel or PEG gel. The adhesive gel or hydrogel helps maintain the bone inducing agent and other medicinal agent in the hollow inner channel of the implant. Further, the bone inducing agent can be injected after the implant is installed to induce bone ingrowth during the post-implantation healing period. The plug-in screw 118 is reinstalled after injection. For bone disease at the implant interface, agents to treat bone disease can be injected using the same procedure as that of the bone inducing agent. Successful bone ingrowth into the cavity of the implant and treatment of bone disease can help avoid failure of implant or avoid additional surgeries.

As shown in FIG. 5, bone inducing agent 153 loaded hydrogel 150 is injected into the implant in a blood analog solution, simulating the implantation of the bone implant. The bone inducing agent is slowly released from the biodegradable hydrogel 150 contained inside the implant (FIG. 5(b)), which provides sufficient time to recruit bone cells on the surface of the implant for initiating osseointegration. In the prior drug delivery systems, the agents are placed on the implant surface, increasing the risk of disruption of the agent through mechanical disturbance during and after the implantation process. The consistent volume and protected hollow inner channel of the current implant system maintains a consistent agent delivery that can be tailed to a specific release file. As bone regeneration into the inner cavity of the implant will integrate the implant, the innovative structure of the side openings of the implant enables of the implant to act as a functional scaffold for bone ingrowth while bearing a masticatory loading.

Further, the implant of the present invention allows the collection of tissue fluid (mostly bone tissue) from the hollow inner channel of the implant any time after implantation without open tissue biopsy. Because the fluid sample represents physiological conditions in the core of the implant site, it can be used to diagnose the progress of bone regeneration and possible pathological symptoms.

Figure 12C:
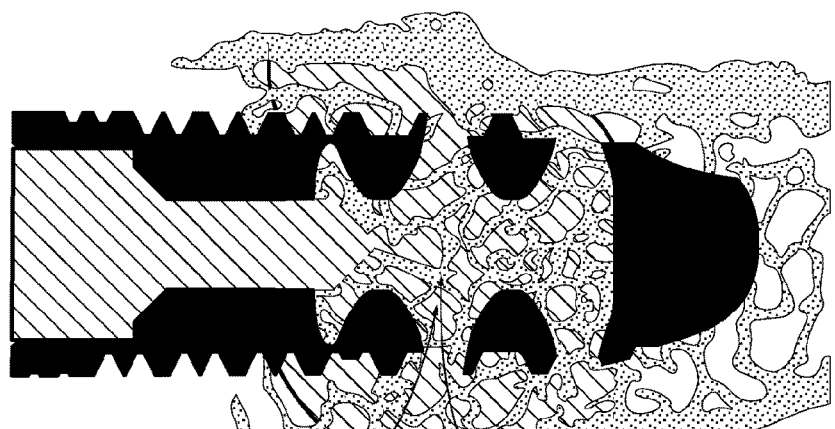
FIG. 12c illustrates the use of the healing cap screw (can also use abutment screw) to prevent blockage from the bone ingrowth into the hollow inner cavity, specifically the subsequent injection of bone inducing agent and/or therapeutic agents through the open spot at the top of the implant after the removal of the healing cap screw 119.
Figure 12B:
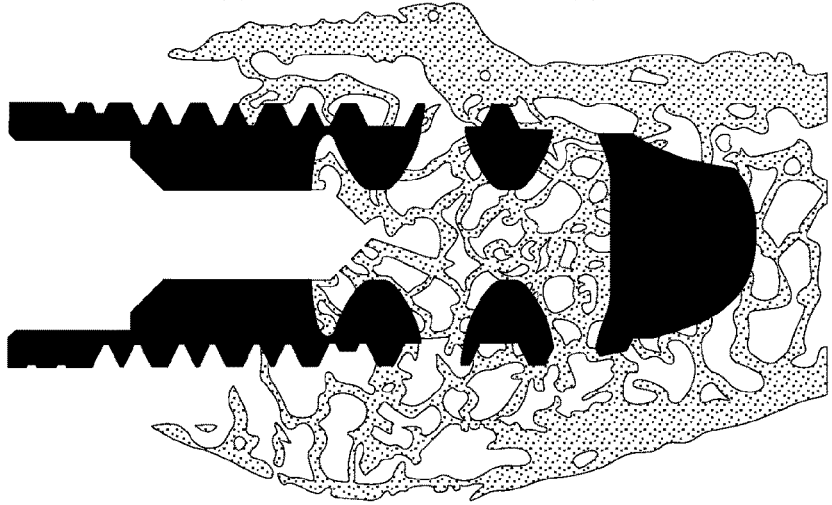
FIG. 12b illustrates the use of the healing cap screw (can also use abutment screw) to prevent blockage from the bone ingrowth into the hollow inner cavity, specifically the removal of the healing cap screw.
Figure 12A:
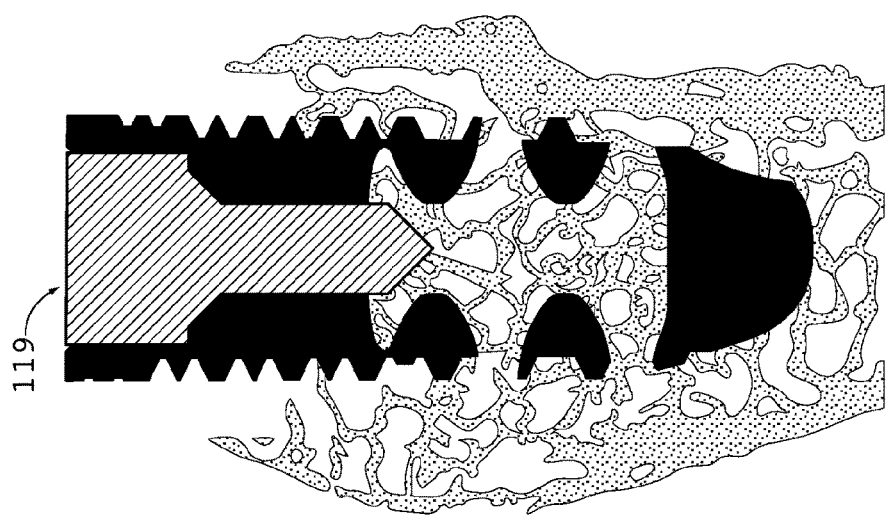
FIG. 12a illustrates the use of the healing cap screw (can also use abutment screw) to prevent blockage from the bone ingrowth into the hollow inner cavity after the addition of a long length of the healing cap screw.

In some embodiments, a long length of healing cap screw is added onto the implant of the present invention as shown in FIG. 12. The long length of the healing cap screw 119 extends to a portion of the hollow inner cavity 110, which will open a pathway through the bone ingrowth (the regenerated bone in the hollow inner channel 110) for the second injection. When later injection of the bone inducing agent or therapeutic agent is needed, the healing cap can be removed (FIG. 12(b)), and then the agent can be injected into the implant (FIG. 12(c)).

Preferred bone morphogenetic proteins (BMPs) are a group of growth factors also known as cytokines and as metabologens. Originally discovered by their ability to induce the formation of bone and cartilage, BMPs are now considered to constitute a group of pivotal morphogenetic signals, orchestrating tissue architecture throughout the body. The important functioning of BMP signals in physiology is emphasized by the multitude of roles for dysregulated BMP signaling in pathological processes.

Recombinant human BMPs (rhBMPs) often are used in orthopedic applications such as spinal fusions, nonunions and oral surgery. rhBMP-2 and rhBMP-7 are Food and Drug Administration (FDA)-approved for some uses. rhBMP-2 causes more overgrown bone than any other BMPs and is widely used off-label.

EXAMPLES

The following examples are illustrative of the invention and are not meant to limit the scope of the invention in any way.

Example 1

Resonance Frequency Analysis (RFA) has been introduced as a non-invasive method to clinically estimate the stability of dental implant systems. The objective of this study was to examine whether implant stability quotient (ISQ) values of RFA can account for mechanical stability of the dental implant system, which is assessed using dynamic mechanical analysis (DMA).

Materials and Methods:

Forty two screw-type titanium dental implants (4.1 mm diameter×10 mm length) were placed in artificial polyurethane foams with 7 different thicknesses (3.5 to 12 mm, 6 individual implants for each thickness). After ISQ values, insertion torque, and static stiffness of each implant system were measured, the DMA (−7±1.5 N at 0.5, 1, 2, 3 Hz) was performed to assess dynamic stiffness and viscoelastic tan δ.

Results and Conclusion:

The ISQ value had strong positive correlations with thickness, insertion torque, static and dynamic stiffness and a negative correlation with tan δ of implant systems in artificial bone blocks (r=0.769 to 0.992, p<0.043). The ISQ values could reflect mechanical stability of the dental implant system.

Example 2

This study examined whether a dental implant system made in part of a highly porous tantalum material can have comparable stability to a traditional threaded implant system, and whether bone would grow into the porous part during post-implantation healing.

Materials and Methods:

Eight healthy 1-year-old male coonhound dogs with permanent dentition were selected because of their anatomical size and bone remodeling characteristics. A threaded, tapered dental implant made of hybrid composition materials, titanium alloy (Ti6A14V), and a highly porous tantalum material was used for the experimental group. The 3-piece dental implant assembly consisted of (1) a threaded titanium cervical section with a smaller diameter central column that extended apically for internal implant support, (2) a porous tantalum shell that fit over the internal central column, and (3) a threaded titanium apical section. A tapered, threaded, titanium alloy implant was used for the control group.

On the days of surgery, antibiotic prophylaxis (amoxicillin p.o., 500 mg. b.i.d.) was initiated 12 hours preoperatively and continued 5 days postoperatively. Animals were sedated with acepromazine (~0.1 mg/kg). After surgery, animals were fed a soft diet for 3 days followed by 1-2 days of weaning back to dry food, and were monitored at least once every 24 hours throughout the study. During the first surgical phase, 4 mandibular premolars (P1-P4) were extracted bilaterally utilizing an atraumatic technique to help preserve the alveolar sockets. The wound sites were sutured for closure and extraction sites were allowed to heal for 3 months. Three days before the second phase surgery, fluoroscopy was used to evaluate extraction site healing. During the second surgical phase, crestal and vertical releasing incisions were made and full-thickness flaps were elevated to expose the alveolar bone in the edentulous areas. Three osteotomies were prepared without a surgical template in the interalveolar margins between the mandibular extraction sites bilaterally. A total of 3 experimental and 3 control implants were placed in each dog utilizing a randomized, reversed or mirrored sequence between each quadrant and between every 2 animals. A total of 48 implants (24 experimental, 24 control) (Ø4.1 mm×13 mm) were used in this study. Immediately after placement, a resonance frequency sensor (SmartPeg®, Osstell AB) was sequentially placed inside each implant and initial implant stability was measured utilizing resonance frequency analysis (RFA) (Ostell Mentor®, Osstell AB). Implant stability was quantified utilizing the values of the RFA unit's proprietary implant stability quotient (ISQ) values. Surgical cover screws were connected to the implants, soft tissues were approximated and primary closure was achieved.

To label newly formed bone tissue, calcein (12.5 mg/kg) was intravenously injected using standard protocols. 23 Animals scheduled for sacrifice after 2 weeks were injected once on day 5 while animals designated for sacrifice at weeks 4, 8 or 12 were injected twice on days 11 and 4 before euthanization. Two animals with mirrored sequences of implant placement were sacrificed via intravenous injection of pentobarbital overdose after 2, 4, 8, and 12 weeks of healing, respectively. Immediately after euthanization, the healing status of the implantation sites was evaluated by fluoroscopy. Implants were then surgically exposed and cover screws were removed from the implants. The RFA analysis was conducted and the resulting ISQ values were recorded. Jaws were then dissected and all study specimens were obtained in block sections.

Each specimen was fixed in a 10% buffered formalin solution, sequentially dehydrated in 70% to 100% ethyl alcohol and xylene, infiltrated, and embedded in methylmethacrylate for un-decalcified sectioning at room temperature. A controlled polymerization procedure was conducted in a cold atmosphere to avoid negative heat influence. After polymerization was substantially completed, 2 undecalcified sections (~100-130 microns thick) were cut in a buccolingual direction along the long-axis of the implant using a diamond wire saw. Both sections were mounted on glass slides for microscopic and histomorphometric evaluations, which were performed by one investigator masked to the specific experimental conditions. One unstained implant section was examined by epifluorescent (for bone labels) and bright field microscopy. The other section was stained with Goldner's Trichrome (GT) to distinguish between mature bone (blue-green) and osteoid, the unmineralized, organic portion of bone matrix that forms prior to the maturation of bone tissue (bright orange) (FIG. 6). Eight images were obtained using a microscope (40×) with dedicated software. Calcein labels were used to evaluate markers of new bone formation. The GT staining enabled bone to be distinguished from osteoid that gradually changes into mineralized bone matrix during the bone maturation process as minerals are deposited into it. All bone-implant surface contact measurements (BIC) were made at the microtextured and machined surfaces of the non-porous implant areas for both groups. In the porous tantalum sections of the experimental group, the percentage of new bone inside the porous material (BTM) was measured using image processing and analysis software (ImageJ®, NIH) to compare the contrast between implant and bone portions in the total porous region.

Results and Conclusion:

All procedures were performed without complications, and implant healing was uneventful. Implants in both study groups remained stable during the healing periods. Average ISQ values were above 60 for control and 65 or above for experimental implants, but these values were not significantly different (p>0.435). Calcein labels and GT staining successfully showed that markers of new bone formation occurred at the bone-implant interface in both control and experimental groups. The BIC did not significantly differ between control and experimental groups at any healing period (p>0.303). Both experimental and control groups did not have significant differences in BIC between healing periods (p>0.095). The BTM values were significantly higher at week 12 than at weeks 2, 4, and 8 (p<0.024).

The range of ISQ values (43.3 to 79.1) measured in the current study were comparable to those previously reported in both human clinical (50 to 65) and canine (59.7 to 89.7) studies. An ISQ value of 60 was equated with clinical implant stability based on the findings of a previous study. The ISQ values recorded at implant placement (baseline) were comparable for both experimental and control implants, and were lower for both groups at all subsequent healing periods. This result could reflect that the newly forming (less mineralized) bone tissue during healing periods produced more compliant mechanical properties of the implant systems.

Histomorphometric analyses showed progressive tissue mineralization inside porous sections from weeks 2 through 12. Porous implants exhibited a combination of progressive osseointegration along their titanium surfaces and bone ingrowth and maturation inside their porous tantalum sections. Apical implant threads, combined with the porous section, were able to stabilize the experimental implant to the same degree as the fully threaded control implant. Further, since bone grew into the porous space of the experimental implant as early as 2 weeks after implantation, it is likely that bone will regenerate 6 weeks after implantation with injected BMP.

Example 3

This study examined how bone tissue mineral distribution is altered by estrogen deficiency-induced active bone remodeling.

Materials and Methods:

Two groups of Sprague-Dawley female rats (6 months old, 288±24 g) were obtained. One rat group received a bilateral ovariectomy (OVX) operation and the other group received a sham operation. After an 8-week post-operation period, the rats were euthanized and vertebrae were obtained. After the removal of all soft tissue and posterior processes, the vertebral specimens were stored at −21° C. until utilization.

After thawing at room temperature, specimens were scanned by a micro-computerized tomography (micro-CT) scanner (SkyScan 1172-D, Kontich, Belgium) with the scanning and reconstruction voxel sizes set at 16×16×16 µm$^3$. The same scanning conditions (49 kV, 200 µA, 0.4° rotation per projection, 8 frames averaged per projection, and 40 ms exposure time) were used for all specimens. Using a calibration curve based on known density phantoms scanned under the same micro-CT conditions, the CT attenuation value (gray value) of each bone voxel was converted to degree of bone mineralization (DBM). Non-bone voxels outside the vertebral cortex were cleaned using a heuristic algorithm, while all voxels inside the vertebral cortex were maintained. The entire three-dimensional (3D) region of vertebral centrum was masked using a compartmentalizing method that we modified based on a procedure used in a previous study to isolate a region of femoral trabecular bone. After bone voxels inside each vertebral image were segmented from non-bone voxels using the heuristic algorithm, bone voxels of the vertebral cortex (CB) were digitally separated from those of the trabecular bone (TB) in the centrum using the masked image of the vertebral centrum. All of the image analysis steps were performed using Image J software (NIH).

The masked volume represented the total volume (TV) of TB. Bone mineral density (BMD) was calculated by dividing the sum of TB DBM by TV. Mean value (Mean) of DBM was computed by dividing the sum of TMD values by the total number of voxels in each region using the TMD histograms of TB and CB. Variability of DBM was represented by the standard deviation (SD) and coefficient of variation (COV), which was computed by dividing the SD by the Mean. Low and high DBM (Low and High) were determined at the lower and upper 5th percentile values, respectively.

Results and Conclusion:

The BMD and TB DBM parameters were significantly higher for the sham group than for the OVX group (p<0.021), except for TBSD and TBCOV, which were significantly lower for the sham group than for the OVX group (p<0.05). While CBmean and CBlow were significantly higher for the sham group than for the OVX group (p<0.016), CBSD, CBCOV and CBhigh were not significantly different between the two groups (p>0.232).

While bone mineral density (BMD) is defined as the mineral content within an apparent volume of bone, including porosity and bone marrow as well as bone matrix, degree of bone mineralization (DBM) represents the mineral content only in the hard tissue of bone. It was shown that the DBM variability of postmenopausal osteoporotic bone increased as a result of estrogen deficiency-induced active bone remodeling. Bone remodeling removes pre-existing (more mineralized) bone tissue while adding immature (less mineralized) bone tissue, and the long-term process of mineralization of the newly formed tissue is started. As such, DBM variability inherently increases while the overall amount of DBM decreases under active bone remodeling. Estrogen deficiency accelerated this process of bone turnover, which is commonly observed in both human and animal bone. Consistent with previous results, we found that TB DBM variability (TBSD and TBCOV) was significantly higher in the OVX group than in the sham group, while the parameters of TB DBM (TBMean, TBlow, and TBhigh) were lower. On the other hand, the CB variability was not significantly different between the two groups, while some parameters of CB DBM (CBMean and CBlow) were significantly lower in the OVX group. These findings indicate that the active bone remodeling triggered by OVX had a greater effect on the TB component of the vertebrae than the CB component by significantly increasing both new bone formation in regions of low mineralization (TBlow) and pre-existing bone resorption in highly mineralized regions (TBhigh) in the OVX TB. Consequently, the TB DBM histogram for the OVX group moved toward lower values than the histogram for the sham group. The higher bone turnover rate in the trabecular bone could arise from the fact that the surface area to be remodeled is larger than that in the cortical bone region.

The results of this study demonstrated that the micro-CT based DBM analysis can account for changes of tissue mineralization resulting from active bone remodeling. As the bone adjacent to an implant is actively remodeled during regeneration, it is likely that its DBM changes. As such, the 3D micro-CT image will be used to distinguish the effects of different BMP doses on DBM distribution adjacent to the implant.

Example 4

Figure 7A:
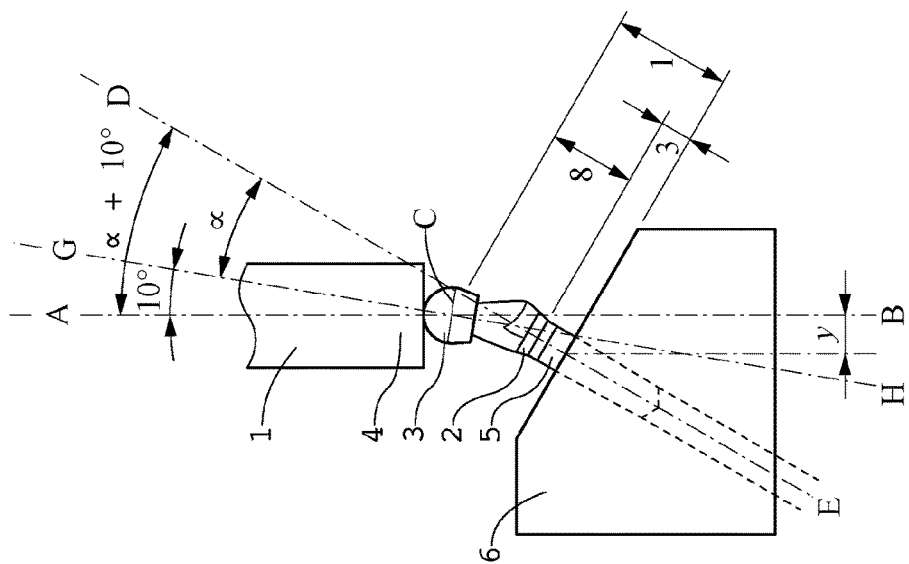
FIG. 7a illustrates results of a fracture test for the implant of FIG. 1, specifically the loading conditions following ISO 14801.
Figure 7B:
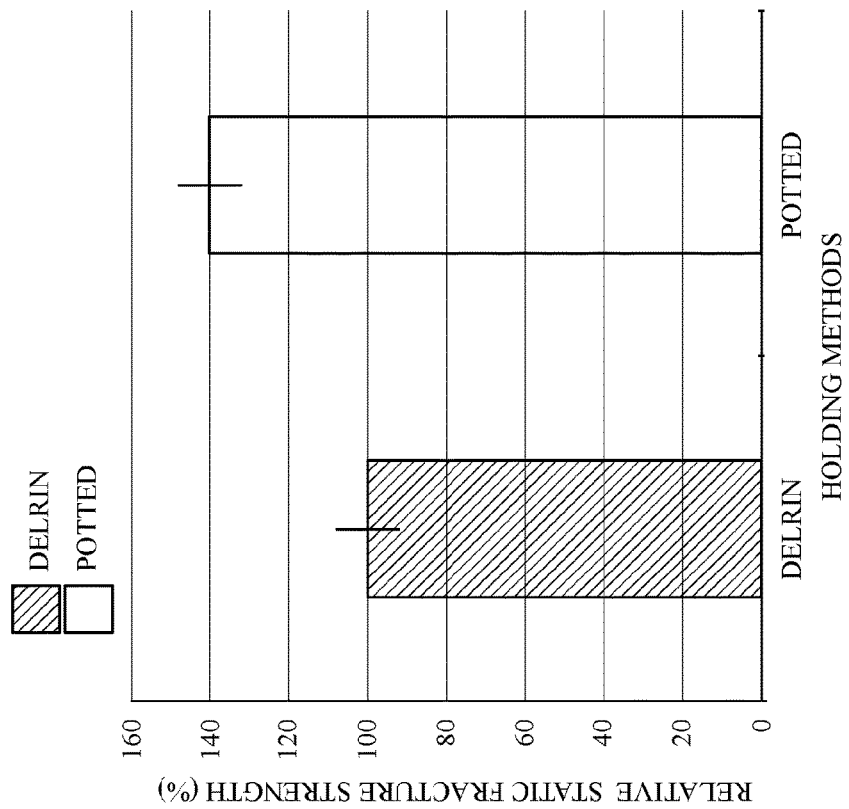
FIG. 7b is a graph that illustrates the relative strength of the implant screwed in Delrin and potted into polymethyl methacrylate (PMMA) bone cement that penetrates into the side openings of the implant during curing.

This study examines the mechanical property of the new implant.—The implant of the present invention at Ø3.5×13 mm with grade 4 titanium. Following international standards for testing the mechanical stability of a dental implant (ISO 14801), the new implants were placed on a loading device (FIG. 7(a)). One group of implants was installed into a resin, after drilling and tapping the polymer resin (Delrin). The other group of implants was potted using polymethyl methacrylate (PMMA) bone cement that penetrates into the side openings of the implant during curing, which simulates regenerated bone tissues after bone ingrowth into the hollow inner channel of the implant. A static compressive force was applied until fracture. The PMMA potted group had significantly higher static strength than the Delrin group ($p<0.005$, n=3 for each group) (FIG. 7(b)).

This mechanical testing result indicates that bone ingrowth into the openings of the implant will increase mechanical stability of the implant system. Fracture occurs at the abutment connection, not within the implant, as usually observed in the traditional solid implant system under a static fracture loading. This result demonstrates that the new implant system is strong enough to bear fracture loading.

Example 5

This study examined the efficacy of the implant of the present invention as a functional scaffolding and for the local delivery of an effective dose of BMP and medication loaded in hydrogel, on whether it can enhance quantity and quality of bone regeneration surrounding the implant without additional surgeries to obtain a biologically and mechanically superior implant system.

Material and Test Techniques
Animal Surgery:

Ten male foxhound dogs (about 2 years old), weighing between 20 and 25 kg will be used. All animals in this study will be cared for in compliance with NIH publication #85-23 and Guide for the Care and Use of Laboratory Animals. The foxhound dog model has been widely accepted in dental implant and bone augmentation related studies.

To create the critical size defect model in each mandible, following sulcular incisions around the mandibular premolars and second molars, a full thickness flap will be elevated and those teeth will be extracted. For the indirect sinus lift model, the posterior maxillary molars will be extracted. These extractions will be conducted bilaterally. The animal care procedures for pre-, at, and post-implantation surgery will follow the same protocol used in the previous study for the dog model in Example 2. All surgeries will be performed at a special operation room in the ULAR. Three months of post-extraction healing will be allowed. The implants will be placed bilaterally in the maxillary sinus, protruding 5 mm into the maxillary sinus, as carried out in previous studies incorporating the sinus lift procedure in a dog mode. Following a buccal incision, full-thickness flaps will be elevated to expose the alveolar bone in the edentulous areas. Osteotomies will be prepared without a surgical template. An initial defect will be created with a 6 mm diameter and a 5 mm depth using a trephine drill. The implantation will be conducted in the defects following the typical surgical process under irrigation. Immediately after placement, a resonance frequency sensor will be sequentially placed inside each implant, and initial implant stability quotient (ISQ) values will be measured utilizing RFA (Ostell Mentor). Tissue fluid will be collected through the inner cavity of the implant. Lyophilized rhBMP-2 will be reconstituted into polyethylene glycol (PEG) hydrogel under sterile conditions. The commercial versions of rhBMP-2 (R&D Systems, Minneapolis, Minn.) and PEG hydrogels (MX-10, Straumann A G, Switzerland) will be purchased. A treatment control (hydrogel without BMP) or rhBMP-2 loaded in the hydrogels will be injected into the individual implants. After surgical cover screws are connected to the implants, the surgical sites will be sutured for closure and allowed to heal. Radiography will be taken at the implantation sites to record baseline (week 0) peri-implant bone levels. To label newly formed bone tissue, alizarin red (30 mg/kg) and calcein green (10 mg/kg) will be intravenously injected 4 and 2 weeks before euthanization, respectively. After 6 and 12 weeks of healing, animals will be sacrificed via intravenous injection of pentobarbital overdose. Tissue fluid will be collected and radiographs will be taken, and ISQ values will be measured at euthanization.

Bone Cell Activity:

Bone cell activity will be assessed by direct measurement of factors released into the internal hollow cavity of the new implant. Enzyme-linked immunosorbent assay (ELISA) will be used throughout the project for both in vitro and in vivo measurements. Five samples will be tested for each parameter. First, levels of released rhBMP2 will be detected with the Human BMP2 ELISA Kit (Sigma-Aldrich). Measurements of osteoblast activity will be assessed using a colorimetric Alkaline Phosphatase Assay Kit (Abcam) and a Canine Osteocalcin ELISA Kit (MyBioSource). Osteoclast activity will be measured using the Dog/Canine C-Telopeptide of Type I Collagen CTX-1 ELISA Kit. In addition, RANKL/OPG ratios will be determined through the use of canine-specific RANKL and OPG ELISA Kits (NeoBiolab). The inflammatory factors will be assessed following the previous study that showed the inflammatory state occurs during peri-implant gingival healing in patients. Commercially available multiplex bead-based assay kits (Bioplex™ Cytokine Assay, Bio-Rad Laboratories) will be used to detect inflammatory factors including TNF-α.

Non-Invasive Dynamic Mechanical Analysis (DMA):

After euthanization, blocks of the bone-implant constructs containing the entire defect region will be dissected and subjected to mechanical testing. After RFA, the bone-implant systems will be mounted on a loading machine with a 450 N load cell and a high resolution (15 nm) displacement transducer. DMA will be performed using four frequencies (0.5, 1, 2, 3 Hz) of cyclic compressive loading at the mean and at amplitudes of −7 N and 3 N for each implant system. This load level is determined to be the minimum magnitude of load needed to obtain a substantially detectable data signal, and the frequency range is comparable to human chewing, which occurs from 0.94 to 2.17 Hz. Following the previous studies, the dynamic stiffness will be measured using dynamic force (F*) and displacement (D*). The dynamic (complex) stiffness (K*) is composed of two parameters: the elastic (storage) stiffness (K') and the viscous (loss) stiffness (K"). A viscoelastic tan δ will also be computed as K"/K'. The elastic and viscous stiffness of a material represents its abilities to store and lose energy, respectively, responding to the applied cyclic loading. As such, the viscoelastic tan δ accounts for efficiency of the material to dissipate energy.

Histomorphological Analysis:

Following the non-destructive DMA, each bone-implant construct will be fixed in a 10% buffered formalin solution and embedded in methylmethacrylate resin. Then, undecalcified sections will be obtained along the long-axis of the implant using a diamond wire saw. The thickness of each section will be less than 200 µm. Epifluorescent microscopy will be used to detect alizarin red and calcein green labels to evaluate new bone formation rates. Following examination of fluorescent labeling, sections will be stained with Masson trichrome to distinguish osteoid, mineralized bone, and the number of osteoblasts and osteoclasts. The bone-implant surface contact (BIC) will be measured along the surface line of the implant thread, and the bone ingrowth inside the inner cavity of the new implant will be quantified using image software.

Micro-CT Based Analysis for Tissue Mineralization:

The sections (~200 µm) of the bone-implant constructs will be prepared next to the sections for histomorphological analysis. The metal implants will be easily removed from the thin sections. Next, the remaining bone parts will be scanned using a micro-CT scanner (SkyScan) with the scanning and reconstruction voxel sizes set at $20 \times 20 \times 20$ µm$^3$. Then, DBM histogram analyses will be performed.

Three Aims (Approaches) of Example 5

Specific Aim 1 (FIG. 8):

Six groups of implant systems will be examined in 5 dogs. Four implants will be placed in the critical size defect sites of each mandible and 2 implants will be placed at the posterior maxillary edentulous sites in each dog. The new implants will be installed in the critical size defects to a depth of half of the length of the implant, resulting in exposure of half of the new implant region that contains side openings. After implantation, 3 concentrations (0.75, 1.5, and 3 mg/ml) of rhBMP-2 (Wyeth Research, Cambridge) loaded in hydrogel and a treatment control hydrogel (the same hydrogel without rhBMP-2) will be injected randomly into the individual implants placed in critical size mandibular bone defects. Also, 0.75 mg/ml of rhBMP-2 loaded in hydrogel (as the effective low dose of rhBMP-2 concentration) and a treatment control (the same hydrogel without rhBMP-2) will be injected randomly into the individual implants at the maxillary edentulous sites. A more than sufficient volume will be injected to fill the inner cavity of the implant (approximately 250 mm$^3$). The 5 animals will be sacrificed after a 6 week period of post-implantation healing.

The sample size is justified based on the results of Example 2 that examined the percentage of bone ingrowth into the porous section of implants (BTM) during healing periods (FIG. 6). The BTMs were 3.32±2.47% at week 2 and 18.69±7.55% at week 12 after implantation in the dog mandibles. For this study, 5 implant specimens for each of 6 groups, for a total of 30 implants in 5 animals, will be used to satisfy the power of statistical analysis.

Planned Data Analysis of Aim 1

Figure 9:
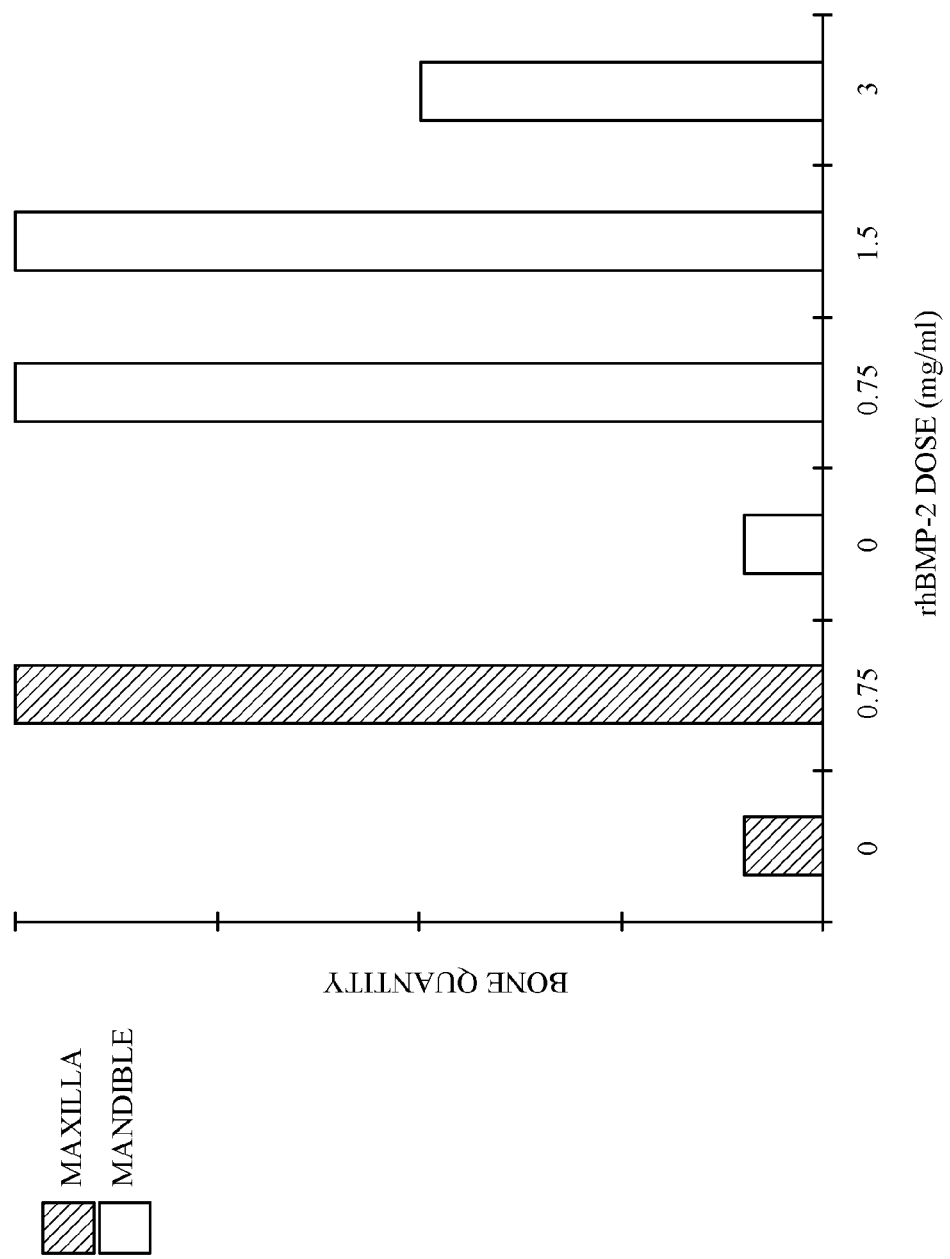
FIG. 9 shows the expected results of bone quantity as related to various doses of the bone inducing agents (such as rhBMP-2 proposed in Example 5) on the bone growth through the use of the implant of FIG. 1.

Effect:

6 implant groups, Variables: Cell activities, rhBMP-2, inflammatory factors, radiography and ISQ values at weeks 0 and 6, DMA parameters, micro-CT based DBM distribution parameters, BIC and percentage of bone ingrowth, bone regeneration rate based on the fluorescence labels, and number of bone cells, Technique:

Repeated measures analysis of variance (RMANOVA) followed by a post hoc test and correlations, Expected Results and Interpretation (FIG. 9):

At 6 weeks post-implantation, the hydrogel will have completely degraded, leaving no remaining concentrations of rhBMP-2, as the degradation time of PEG hydrogel was measured to be 15 days in vitro. Substantial bone regeneration will be observed in the critical size defects surrounding and inside the implants injected with the rhBMP-2, while no spontaneous bone regeneration will occur in the critical size defect with the control implant group. However, the regenerated bone from 3 mg/ml of rhBMP-2 will have immature characteristics with more active bone cells that produce faster bone turnover, less bone quantity with higher porosity, less BIC, and worse bone quality with less mineralized bone tissue resulting in a smaller ISQ value and lower static and dynamic stiffness. The bone will also have higher values of viscoelastic tan δ than that regenerated from other rhBMP-2 doses. We also expect that inflammatory reactions may be triggered by the high dose of rhBMP-2. It was observed that inflammation, exaggerated by BMP-2 in absorbable collagen sponges, produces greater numbers of osteoclasts and increased osteoclast activity while reducing osteoblastic differentiation. This observation likely accounts for porous and immature bone regeneration adjacent to implants treated with high doses of rhBMP-2. The 0.75 mg/ml of rhBMP-2 dose will successfully regenerate sufficient quantity and quality of bone around the implants in the mandibular defects and elevate the sinus floor. These results will suggest that using 0.75 mg/ml of rhBMP-2 as a low dose of rhBMP-2 will produce relevant bone regeneration, sinus floor elevation, and osseointegration. Assays of cellular activities will support these findings. It is expected that the low dose of rhBMP-2 will stimulate increased levels of alkaline phosphate and osteocalcin (measurements of osteoblast activity), with minimum activation of CTX and RANKL/OPG levels (measurements of osteoclast activity).

Overall, increases in osteoblastic activity will produce greater quantities of bone visible radiographcally and greater ISQ values of the implant system measured in vivo, which will have positive correlations with the number of osteoblasts, mineralization, and the mechanical properties of the implant system measured in vitro.

Specific Aim 2 (shown in FIG. 8):

Additional 5 dogs will be obtained. Four implants will be placed bilaterally in 4 critical size defect sites in each dog mandible. After implantation, 2 treatment control hydrogels (the same hydrogel without rhBMP-2) and 2 concentrations (0.375 and 0.75 mg/ml) of rhBMP-2 loaded in the hydrogel will be injected randomly into the individual implants placed at the critical size mandibular bone defects. After a period of 6 weeks of post-implantation healing, a minimal incision will be made to open each healing cap and the second injections will be given.

For the 2 implant systems that were injected with the control hydrogel, after 6 weeks of healing, one will be injected again with the same control hydrogel and the other will be injected with 0.75 mg/ml of rhBMP-2 loaded in hydrogel, and each will be allowed to heal for an additional 6 weeks. Thus, this model will simulate the clinical case of severe marginal bone loss adjacent to the implant in function and its treatment using a therapeutic agent that can be injected into the new implant system. For the other 2 implant systems injected with rhBMP-2 in hydrogel, after 6 weeks of healing the same dose of rhBMP-2 will be injected again and the site will be allowed to heal for an additional 6 weeks. This sequence of injections is designed to examine which frequency or total injection dose is more likely to stimulate bone regeneration. All surgical and experimental procedures will be the same as those utilized in Aim 1. The 5 animals will be sacrificed after a period of 12 weeks of post-implantation healing. The sample size (5 implants for each group) is justified in Aim 1.

Planned Data Analysis

Effect:

4 implant groups at each healing period, Variables: Cell activities, rhBMP-2, inflammatory factors, radiography and ISQ values at weeks 0, 6 and 12, DMA parameters, micro-CT based DBM distribution parameters, BIC and percentage of bone ingrowth, bone regeneration rate based on the fluorescence labels, and number of bone cells, Technique: Repeated measures analysis of variance (RMANOVA).

Figure 10:
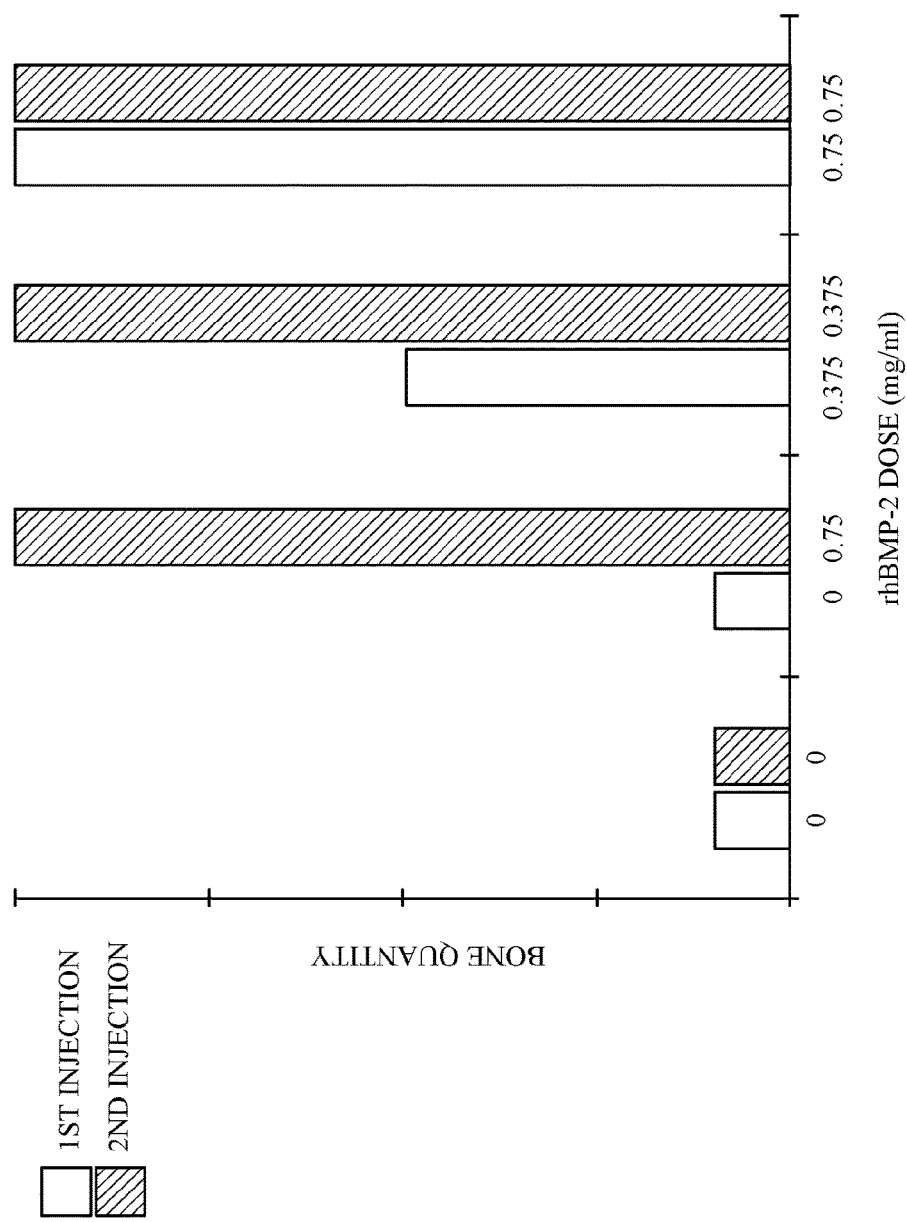
FIG. 10 illustrates the expected results of two injections of the bone inducing agents (such as rhBMP-2 in Example 5) on the bone growth through the use of the implant of FIG. 1.

Expected Results and Interpretation (FIG. 10):

At 6 and 12 weeks after implantation, the hydrogel will have completely degraded, leaving no remaining concentrations of rhBMP-2, as the degradation time of PEG hydrogel was measured to be 15 days in vitro. The delayed injection of rhBMP-2 in the hydrogel at week 6 will effectively induce bone regeneration in the critical size bone defects around the implant while a lack of bone regeneration will occur without rhBMP-2. The booster injection with a lower dose of rhBMP-2 will produce more bone regeneration around the implant than the delayed injection, but less than the higher dose injection. This result will arise from the fact that, although the initial dose of rhBMP-2 is fully released with completion of the hydrogel degradation prior to the booster injection at week 6 after implantation, effects from the initial dose on bone formation will continue because the period of bone formation in dogs is longer than 10 weeks. Thus, the booster injection will activate additional bone remodeling that adds to the quantity of already regenerated bone around the implant. The higher dose of rhBMP-2 (0.75 mg/ml) will accelerate the bone turnover rate, resulting in a faster increase in bone quantity around the implant than the low dose (0.375 mg/ml). Thus, outcomes from the current project will support the idea that the biological and mechanical stability of the implant system will be significantly improved by post-implantation treatments without the cost of additional painful surgeries.

Aim 3:

A mouse myoblast cell line (C2C12) that converts to the osteoblast lineage in the presence of BMP2 will be obtained (ATCC, Manassas). 30,000 C2C12 cells will be plated in 24-well plates in Dulbecco's Modified Eagle's medium (DMEM) containing 10% fetal bovine serum (FBS), and will be allowed to adhere overnight. Sterilized implants will be installed through specially fabricated lids for the 24-well plates locating an implant in each well. The part of each implant with openings will be submersed into the culture media while the upper region will be kept above the lid, exposing the top opening.

Figure 8:
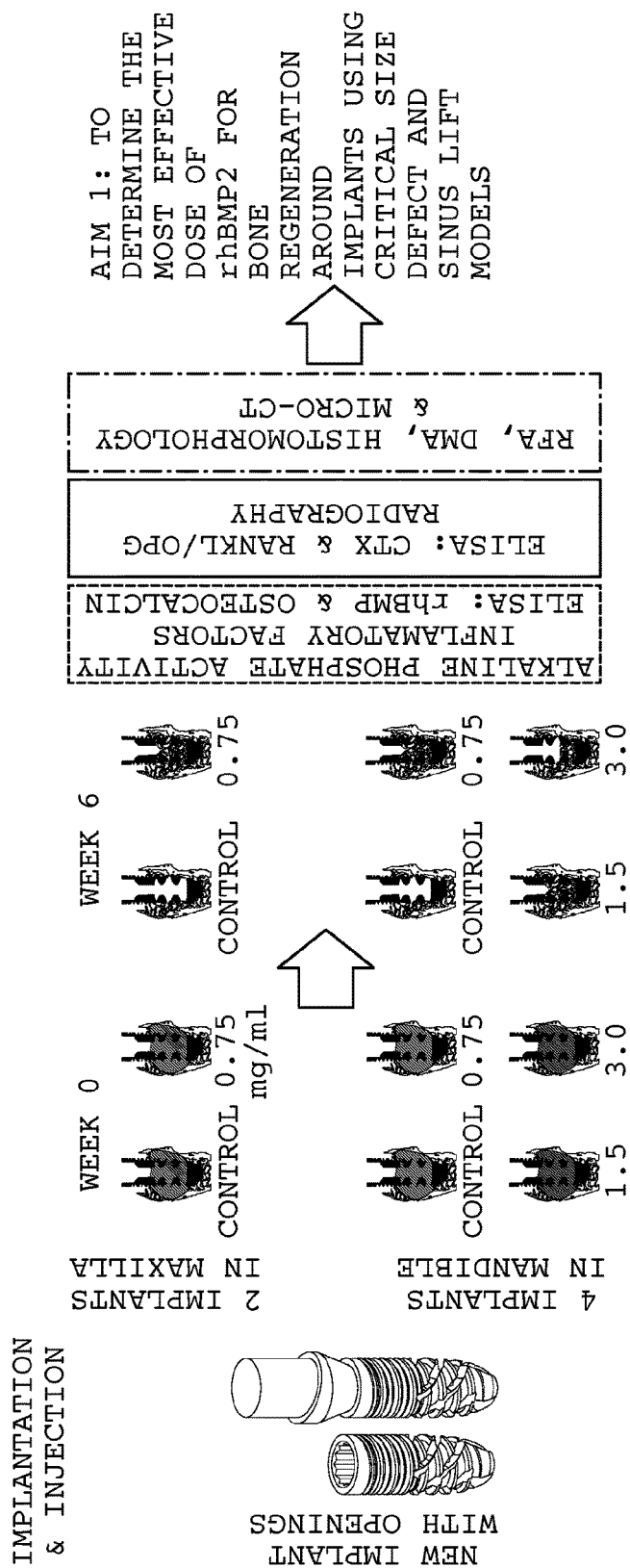
FIG. 8 illustrates the experimental process for Aims 1 to 3 of Example 5: Aim 1 is to determine the most effect dose of bone inducing agents for bone regeneration around the implants using critical size defect and sinus lift models by using different concentrations of bone inducing agents; Aim 2 is to evaluate effects of delayed and booster injections of bone inducing agents; and Aim 3 is to examine efficacy for a local delivery of the therapeutic agents.
Figure 8:
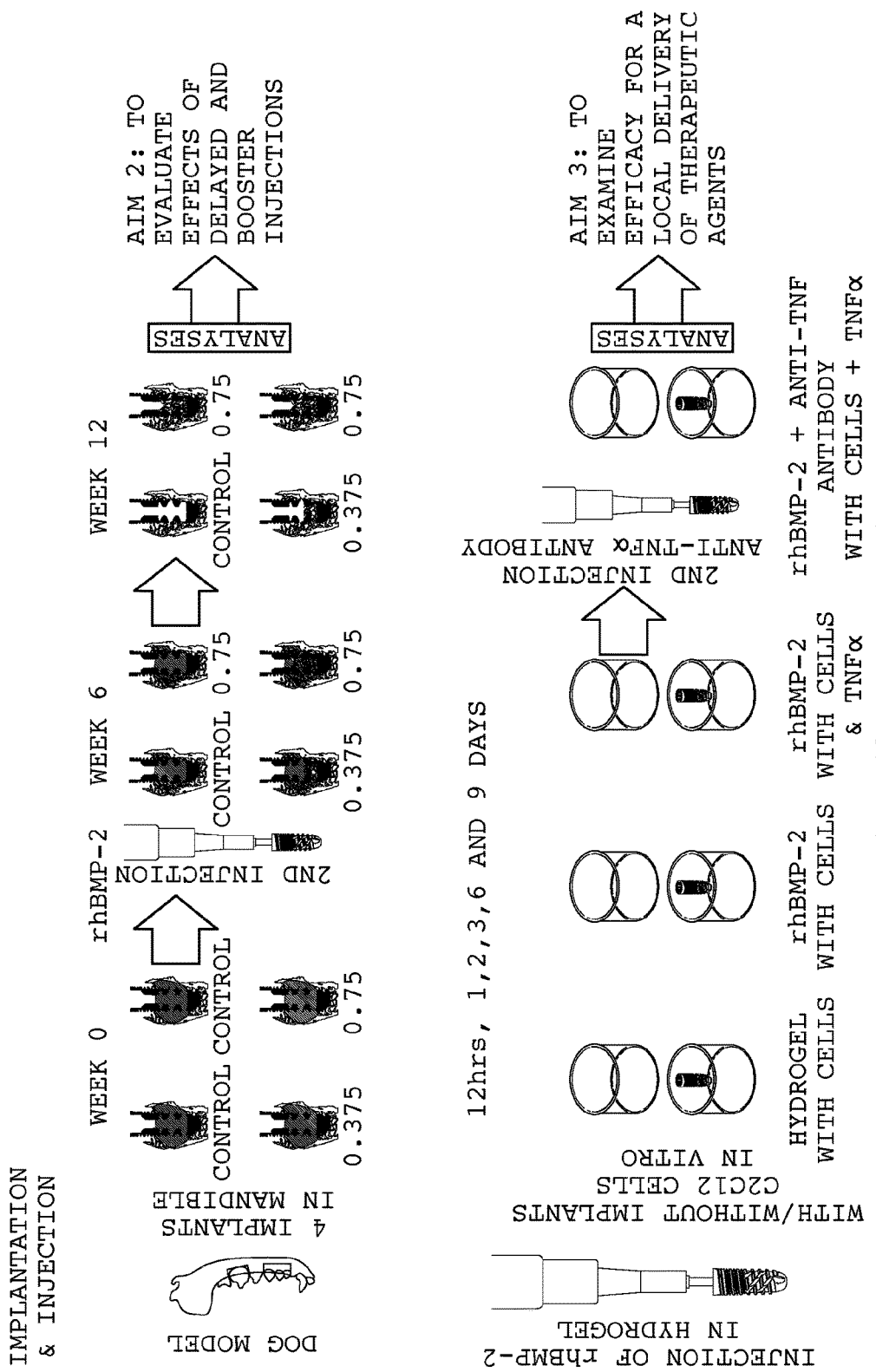

The rhBMP-2 (100 ng/ml) will be reconstituted into the PEG hydrogel. For the purpose of comparison, 4 groups will be examined (FIG. 8). The first group will be a control group in which hydrogel without rhBMP-2 will be injected into the implant, which will be maintained in a culture with C2C12 cells. For the second group, hydrogel with rhBMP-2 will be injected into the implant and cultured with C2C12 cells, causing induction of osteoblastic differentiation. For the third group, the hydrogel with rhBMP-2 will be injected into the implant and cultured with C2C12 cells in the presence of TNF-α (10 ng/ml) (PeproTech), which has been demonstrated to suppress osteoblastic differentiation. The proposed dose of TNF-α is higher than the maximum concentration in blood serum measured in the exaggerated inflammatory environment after placing BMP-2 in an animal model (700 pg/ml). The fourth group will be set up the same as the third group, except that anti-TNFα antibody (8 ug/ml; Abcam, Cambridge) will also be added to the hydrogel. To date, there has been a lack of investigation into the effects of anti-TNF-α therapeutics on suppressed osteoblastic differentiation caused by TNF-α. The current study will test whether administration of the antibody will inhibit TNF-α's activity in the culture medium, thus allowing osteoblast differentiation. Fresh cell culture medium in the well plates will be replaced at 12 hours, and days 1, 2, 3, 6, and 9 after injections. The replaced culture media will be used to assess the released amounts of rhBMP-2 and anti-TNFα antibody, remaining levels of the TNF-α, and parameters resulting from cell activities, including alkaline phosphatase (ALP) activity and osteocalcin levels. The parameters to be assessed will be determined depending on the treatment conditions for each group. The same assay kits used for Aims 1 and 2 will be utilized to assess parameters. A TNFα-directed ELISA (R&D Systems, Minneapolis) will be used to quantify the release of the anti-TNFα antibody. In addition, four control groups will be created with the same treatments, but without the implants. The same analyses that will be performed for the implantation groups will be used for these control groups to examine the role of the implant in controlling the release rates of the agents.

The sample size is estimated using the previous study that compared the ALP activity between incorporating TNF-α in the culture media of C2C12 cells with BMP-2 and not incorporating TNF-α in the culture media. The levels of ALP activity were 2.0±0.2 with TNF-α and 10.9±1.8 without TNF-α. Based on this previous result, we computed that 3 specimens will be the minimum number of samples needed to obtain a significant result ($p<0.05$) with 95% statistical power for determining the effect of TNF-α. Thus, for the current project, we propose 5 samples for each group, for a total of 240 specimens (5 specimens×4 groups×6 times×with/without implants), to satisfy the power of statistical analysis.

Planned Data Analysis

Figure 11:
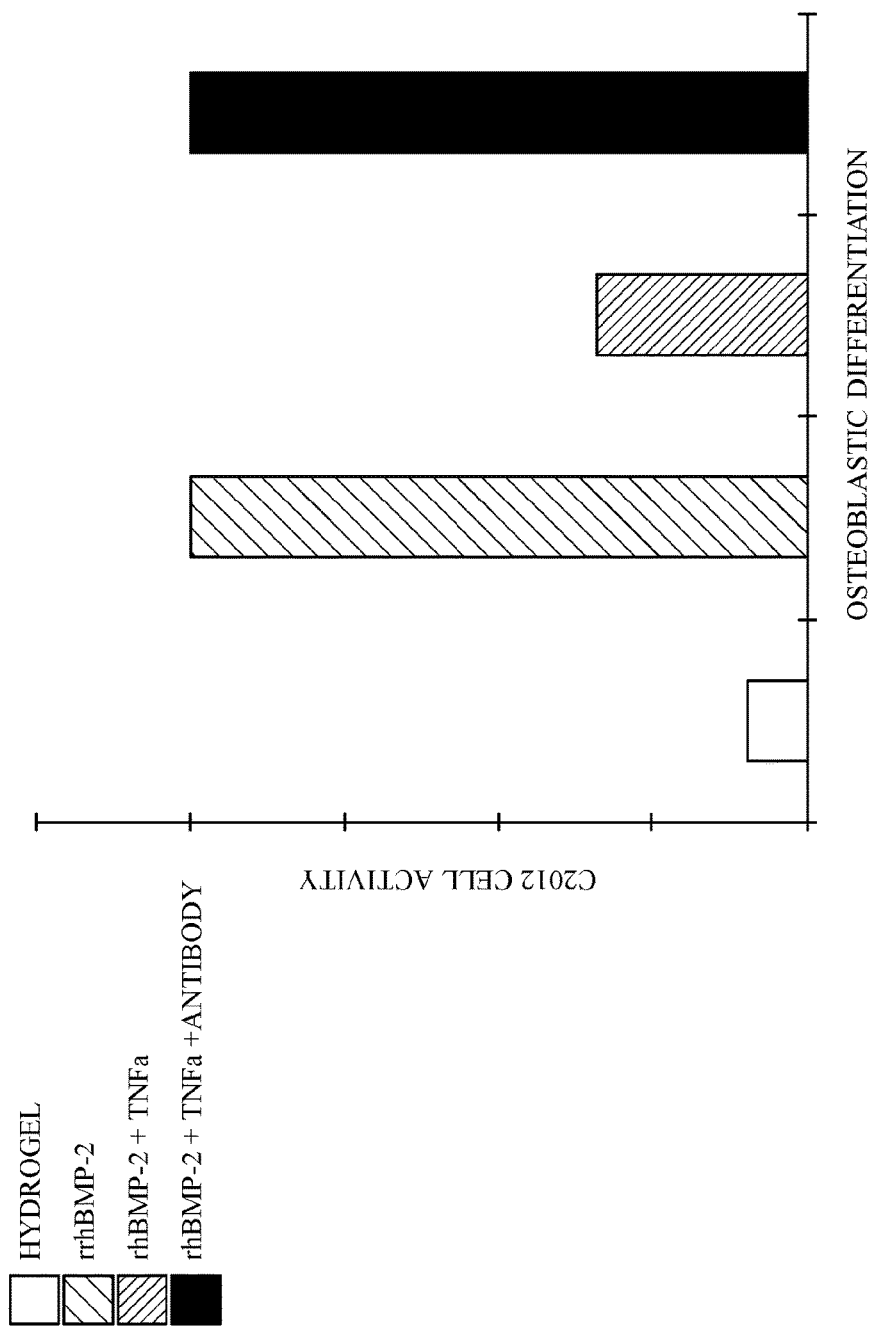
FIG. 11 illustrates the expected efficacies of the local delivery of anti-inflammatory agent when it is combined with the use of the bone inducing agent (such as rhBMP-2 in Example 5) on the bone forming cell (osteoblast) differentiation by using the implant of FIG. 1.

Effect:

Sampling times, Variables: rhBMP-2, TNF-α, anti-TNFα antibody, ALP activity, and osteocalcin, Technique:

Repeated measures analysis of variance (RMANOVA) followed by a post hoc test,

Expected Results and Interpretation (FIG. 11):

The released amount of rhBMP-2 will reach its peak level within one day after injection, as observed in the previous study. The rhBMP-2 will be released both from hydrogel only and from hydrogel injected into the implant. It is expected that rhBMP-2 released from either system will be sufficient to stimulate osteoblastic differentiation of C2C12 cells in vitro, and that both alkaline phosphatase and osteocalcin levels will start to increase 2-3 days after the addition of rhBMP-2, as observed in the previous study. The suppression and treatment of osteoblastic differentiation by TNF-α and anti-TNFα antibody will be observed, respectively. This result will provide insight into the observation that the rhBMP-2 overdose related inflammatory reaction can reduce osteoblastic differentiation, producing immature bone regeneration. For development of an efficient treatment strategy, associations of the release profiles of rhBMP-2 and anti-TNFα antibody with C2C12 cell activities will be identified. These findings will validate the efficacy of the implant for local delivery of therapeutic agents without additional surgeries following implantation.

Potential Difficulties and Alternative Strategies

A lack of bone ingrowth into the internal hollow cavity of the new implant and weak mechanical stability might be observed, as seen with the commercial Core-Vent and hollow implant with open apical systems. The present new implant is significantly different from the hollow type implants because injection of effective agents through the inner cavity of the implant is allowed, which induces bone ingrowth. In addition, its closed bottom portion maintains stable mechanical strength, as shown in FIGS. 1 to 4.

The bone ingrowth into the inner cavity might block the connection to the top opening. While the full ingrowth of bone will enhance mechanical stability of the new implant system, it might inhibit the ability to inject an agent through the inner pathway. A longer healing cap screw can be used, one that extends to the top portion of the inner cavity, which will open a pathway through the bone ingrowth for the second injection (FIG. 12).

As the implant systems will be placed in the jaw bone of the same animal, the results from a specific implant site might be influenced by a different concentration of rhBMP-2 at adjacent implant sites. The implantations will be implemented bilaterally and separated by $4^{th}$ premolars on the same side of each mandible, which will help minimize the interactive effects between the different doses of rhBMP-2.

The sinus floor might not be high enough to place implants for indirect sinus elevation. The main purpose of this aim will be to examine whether the new implant system can produce effective bone regeneration in the maxillary floor. Thus, alternatively, a direct sinus elevation can simultaneously lift the Schneiderian membrane and then induce bone regeneration by rhBMP-2 injection through the new implant system.

Significant spontaneous bone regeneration might occur around the control implant systems. Since all parameters assessed in this project will be quantified, the results will still be able to be evaluated by comparing the magnitudes of measures for any regenerated bone.

While inflammatory cytokine increases osteoclastic activities as well as inhibits BMP-2 induced osteoblastic differentiation, analyses for the osteoclasts will not be included because induction of BMP2-responsive cell differentiation in vitro will properly validate efficacy of the new implant system for drug delivery.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A hybrid dental implant comprising:
a dental implant body having an external thread on an external surface of the dental implant body, the dental implant body having a length of 15.0 mm or less and a diameter of 5.0 mm or less,
the dental implant body comprising an upper portion with an open ceiling, a middle portion having a hollow inner channel, and a lower portion with a closed floor;
the hollow inner channel comprising
a) one portion connected to the open ceiling, which is configured to receive one or more injectable bone inducing agents;
b) a lower portion terminating at the closed floor; and
c) one or more side openings extending from the hollow inner channel, rotating in a helix-like shape in an opposing direction from that of a plurality of turns of the external thread, wherein the dimensions of the side openings are of sizes designed to enable bone ingrowth into the hollow inner channel and bone outgrowth from the hollow inner channel to the surrounding bone.

2. The hybrid dental implant in accordance with claim 1, wherein the upper portion, the middle portion and the lower portion of the dental implant body located successively along the length of the dental implant body in a longitudinal direction, the upper portion occupying the upper 40% to 50% of the length of the dental implant body, the adjacent middle portion occupying the middle 40% to 50% of the length of the dental implant body, and the lower portion is adjacent to the middle portion, occupying the lower 10 to 20% of the lower or bottom portion of the length of the dental implant body.

3. The hybrid dental implant in accordance with claim 1, wherein the hollow inner channel has a diameter in the range of about 0.5 mm to about 2.0 mm.

4. The hybrid dental implant in accordance with claim 1, wherein the one or more side openings have a width on a surface of the dental implant body in the range of about 0.6 mm to about 1.5 mm.

5. The hybrid dental implant in accordance with claim 1, further comprising a plug-in screw, a healing cap screw, or an abutment screw connected to the open ceiling, extending into the hollow inner channel.

6. The hybrid dental implant in accordance with claim 1, wherein the lower portion comprises one or more self-tapping cuts at a front end of the lower portion.

7. The hybrid dental implant in accordance with claim 1, wherein the bone inducing agent includes bone morphogenetic proteins.

8. The hybrid dental implant in accordance with claim 1, further comprising a hydrogel loaded with bone inducing agents.

9. The hybrid dental implant in accordance with claim 8, further comprising one or more therapeutic agents.

10. A method for installing a hybrid dental implant into a bone, the method comprising:
a) screwing a hybrid dental implant with a dental implant body having at least one external thread into a bored hole in the bone, the dental implant body having a length of 15.0 mm or less and a diameter of 5.0 mm or less; and
b) injecting a suitable amount of bone inducing agent loaded hydrogel into an open ceiling of the implant, thereby delivering the hydrogel into an upper portion of the implant, whereby the hydrogel moves into a hollow inner channel in a middle portion of the implant with one or more side openings extending from the hollow inner channel, rotating in a helix-like shape in an opposing direction from that of a plurality of turns of the external thread, wherein the one or more side openings extend from a beginning end of the middle portion to a lower end of the middle portion, and through which the bone inducing agent enables bone ingrowth into the hollow inner channel.

11. The method in accordance with claim 10, further comprising a step of injecting medicinal or therapeutic agent into the hollow inner channel.

12. The method in accordance with claim 10, further comprising steps of waiting for a period of time after implantation, and injecting one or more doses of bone inducing agents in the hydrogel into the hollow inner channel.

13. The method in accordance with claim 10, further comprising a step of introducing one or more therapeutic agents into the hollow inner channel of the implant during the implantation.

14. The method in accordance with claim 10, further comprising a step of introducing one or more therapeutic agents into the hollow inner channel of the implant after the implantation.

15. A hybrid dental implant comprising:
a dental implant body having an external thread on an external surface of the dental implant body, the dental implant body having a length of 15.0 mm or less and a diameter of 5.0 mm or less,
the dental implant body comprising an upper portion with an open ceiling, a middle portion having a hollow inner channel, and a lower portion with a closed floor;
the hollow inner channel comprising
   a) one portion connected to the open ceiling, which is configured to receive one or more injectable bone inducing agents;
   b) a lower portion terminating at the closed floor; and
   c) one or more side openings extending from the hollow inner channel, rotating in a helix-like shape in an opposing direction from that of a plurality of turns of the external thread, wherein the dimensions of the one or more side openings are of sizes designed to enable bone ingrowth into the hollow inner channel and bone outgrowth from the hollow inner channel to the surrounding bone, wherein the one or more side openings extend from a beginning end of the middle portion to a lower end of the middle portion.

\* \* \* \* \*